(12) United States Patent
Zhang et al.

(10) Patent No.: US 9,518,038 B2
(45) Date of Patent: Dec. 13, 2016

(54) CONDENSATION PRODUCT OF THEANINE DERIVATIVE AND CARBOXYLIC ACID COUMARIN DERIVATIVE, ITS INTERMEDIATE, PREPARATION METHOD AND USE THEREOF

(71) Applicant: SHANDONG YINGDONG YINGHAO BIOTECHNOLOGY, INC., Yantai (CN)

(72) Inventors: Guoying Zhang, Yantai (CN); Ying Zhang, Yantai (CN); Benhao Wu, Yantai (CN); Guohua Zhang, Yantai (CN)

(73) Assignee: Shandong Yingdong Yinghao Biotechnology, Inc. (CN)

( * ) Notice: Subject to any disclaimer, the term of this patent is extended or adjusted under 35 U.S.C. 154(b) by 0 days.

(21) Appl. No.: 14/431,707

(22) PCT Filed: Sep. 25, 2013

(86) PCT No.: PCT/CN2013/084146
§ 371 (c)(1),
(2) Date: Mar. 26, 2015

(87) PCT Pub. No.: WO2014/048313
PCT Pub. Date: Apr. 3, 2014

(65) Prior Publication Data
US 2015/0239861 A1    Aug. 27, 2015

(30) Foreign Application Priority Data

Sep. 27, 2012   (CN) .......................... 2012 1 0363366
Sep. 27, 2012   (CN) .......................... 2012 1 0363367
(Continued)

(51) Int. Cl.
*A01N 43/16*   (2006.01)
*A61K 31/355*   (2006.01)
(Continued)

(52) U.S. Cl.
CPC ........... *C07D 311/12* (2013.01); *A61K 31/223* (2013.01); *A61K 31/37* (2013.01); *C07C 229/22* (2013.01);
(Continued)

(58) Field of Classification Search
USPC .......................................... 514/458; 424/450
See application file for complete search history.

(56) References Cited

U.S. PATENT DOCUMENTS 4,317,774 A    3/1982   Sassiver et al.

FOREIGN PATENT DOCUMENTS

| CN | 101484430 | 7/2009 |
|---|---|---|
| CN | 103110621 | 5/2013 |
| WO | 2009/089508 | 7/2009 |

OTHER PUBLICATIONS

PCT/CN2013/084146 International Search Report dated Jan. 16, 2014.
(Continued)

*Primary Examiner* — Marcos Sznaidman
(74) *Attorney, Agent, or Firm* — Honigman Miller Schwartz and Cohn LLP; Thomas A. Wootton, Esq.; Jonathan P. O'Brien

(57) ABSTRACT

The present invention relates to a compound as represented by formula (I), which is a condensation product of a theanine derivative and a carboxylic acid coumarin derivative, compounds as represented by formula (II) and formula (III), both of which are intermediates of the condensation product, a method for preparing these compounds, a pharmaceutical composition comprising the compounds, and a use thereof in preparing a medicament for prevention and treatment of tumors, inflammation, cardiovascular diseases, immune deficiency diseases and the like.

Formula (I)

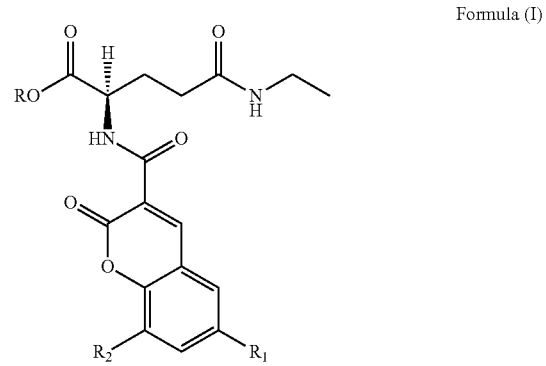

Wherein,

| (Ia) | R=CH$_3$ | R$_1$=H | R$_2$=H |
|---|---|---|---|
| (Ib) | R=CH$_2$CH$_3$ | R$_1$=H | R$_2$=H |
| (Ic) | R=CH$_2$CH$_3$ | R$_1$=Cl | R$_2$=H |
| (Id) | R=CH$_2$CH$_3$ | R$_1$=Br | R$_2$=H |
| (Ie) | R=CH$_2$CH$_3$ | R$_1$=F | R$_2$=H |
| (If) | R=CH$_2$CH$_3$ | R$_1$=NO$_2$ | R$_2$=H |
| (Ig) | R=CH$_2$CH$_3$ | R$_1$=Cl | R$_2$=Cl |
| (Ih) | R=CH$_2$CH$_3$ | R$_1$=Br | R$_2$=Br |
| (Ii) | R=CH$_2$CH$_3$ | R$_1$=NH$_2$ | R$_2$=H |

(Continued)

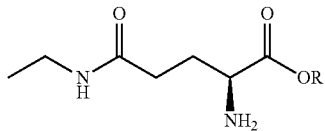

Formula (II)

Wherein,

| (IIa) | R=CH$_3$ |
| --- | --- |
| (IIb) | R=CH$_2$CH$_3$ |

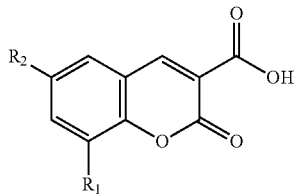

Formula (III)

Wherein,

| (IIIc) | R$_1$=Cl | R$_2$=H |
| --- | --- | --- |
| (IIId) | R$_1$=Br | R$_2$=H |
| (IIIe) | R$_1$=F | R$_2$=H |
| (IIIf) | R$_1$=NO$_2$ | R$_2$=H |
| (IIIg) | R$_1$=Cl | R$_2$=Cl |
| (IIIh) | R$_1$=Br | R$_2$=Br |

9 Claims, 1 Drawing Sheet

(30) Foreign Application Priority Data

| Sep. 27, 2012 | (CN) | ............... 2012 1 0363369 |
| --- | --- | --- |
| Sep. 27, 2012 | (CN) | ............... 2012 1 0363378 |
| Dec. 6, 2012 | (CN) | ............... 2012 1 0515826 |
| Dec. 6, 2012 | (CN) | ............... 2012 1 0515827 |
| Jan. 28, 2013 | (CN) | ............... 2013 1 0030234 |

(51) Int. Cl.

| A61K 9/127 | (2006.01) |
| --- | --- |
| C07D 311/12 | (2006.01) |
| C07C 237/06 | (2006.01) |
| A61K 31/223 | (2006.01) |
| A61K 31/37 | (2006.01) |
| C07D 311/74 | (2006.01) |
| C07C 229/22 | (2006.01) |

(52) U.S. Cl.
CPC ........... *C07C 237/06* (2013.01); *C07D 311/74* (2013.01); *C07B 2200/07* (2013.01)

(56) References Cited

OTHER PUBLICATIONS

Aimin Song; A convenient synthesis of coumarin-3-carboxylic acids via Knoevenagel condensation of Meldrm's acid with ortho-hydroxyaryl aldehydes or ketones, Tetrahedron Letters, 2003, 44, 1755-1758.

Xiu-hong Liu; L-Proline as an efficient and reusable promoter for the synthesis of coumarins in ionic liquid, J. Zhejiang Univ. Sci. B, 2008, 9, 12, 990-995.

Daniela Secci; Synthesis and selective human monoamine oxidase inhibition of 3-carbonyl, 3-acyl, and 3-carboxyhydrazido coumarin derivatives, European Journal of Medicinal Chemistry, 2011, 46, pp. 4846-4852.

Chimenti et al., "Inhibition of monoaminen oxidases by coumarin-3-acyl derivatives: biological activity and computational study", Bioorganic & Medicinal Chemistry Letters, 14:3697-3703, 2004.

Creaven et al., "Synthesis, characterization and antimicrobial activity of a series of substituted coumarin-3-carboxylatosilver(I) complexes", Inorganica Chimica Acta, 359:3976-3984, 2006.

Irvine et al., "Coumarin-3-carboxylic acid derivatives as potentiators and inhibitors of recombinant and native N-methyl-D-aspartate receptors", Neurochemistry International, 61(4):593-600, 2012.

Liu et al., "L-Proline as an efficient and reusable promoter for the synthesis of coumarins in ionic liquid", Journal of Zhejiang Univ. Sci. B, 9(12):990-995, 2008.

Liu et al., "Biological evaluation of coumarin derivatives as mushroom tyrosinase inhibitors", Food Chemistry, 135:2872-2878, 2012.

Peng et al., "Facile synthesis of 4-substituted 3,4-dihydrocoumarins via an organocatalytic double decarboxylation process", Organic & Biomolecular Chemistry, 10:2537-2541, 2012.

Secci et al., "Synthesis and selective human monoamine oxidase inhibition of 3-carbonyl, 3-acyl, and 3-carboxyhydrazido coumarin derivatives", European Journal of Medicinal Chemistry, 46:4846-4852, 2011.

Silverman, The Organic Chemistry of Drug Design and Drug Action (Second Edition), Chapter 2, pp. 19-20, 2007.

Song et al., "A convenient synthesis of coumarin-3-carboxylic acids via Knoevenagel condensation of Meldrum's acid with ortho-hydroxyaryl aldehydes or ketones", Tetrahedron Letters, 44:1755-1758, 2003.

Thati et al., "Retracted: In vitro anti-tumour and cyto-selective effects of coumarin-3-carboxylic acid and three of its hydroxylated derivatives, along with their silver-based complexes, using human epithelial carcinoma cell lines", Cancer Letters, 248(2):321-331, 2007.

Vuong et al., "L-Theanine: properties, synthesis and isolation from tea", J Sci Food Agric, 91:1931-1939, 2011.

Watson and Christiansen, "Solid Phase Synthesis of Substituted Coumarin-3-Carboxylic Acids via the Knoevenagel Condensation", Tetrahedron Letters, 39(33):6087-6090, 1998.

Brett T. Watson and Gerda E. Christiansen, "Solid Phase Synthesis of Substituted Coumarin-3-Carboxylic Acids via the Knoevenagel Condensation", Tetrahedron Letters, 39(33):6087-6090, 1998.

Shiyong Peng et al., "Facile synthesis of 4-substituted 3,4-dihydrocoumarins via an organocatalytic double decarboxylation process", Organic & Biomolecular Chemistry, 10:2537-2541, 2012.

R. O. Clinton and S. C. Laskowski, "Coumarins. I. Derivatives of Coumarin-3- and 4-Carboxylic Acids", J. Am. Chem. Soc., 71:3602-3606, 1949.

Yasuyuki Sadzuka et al., "Enhancement of the activity of doxorubicin by inhibition of glutamate transporter", Toxicology Letters, 123:159-167, 2001.

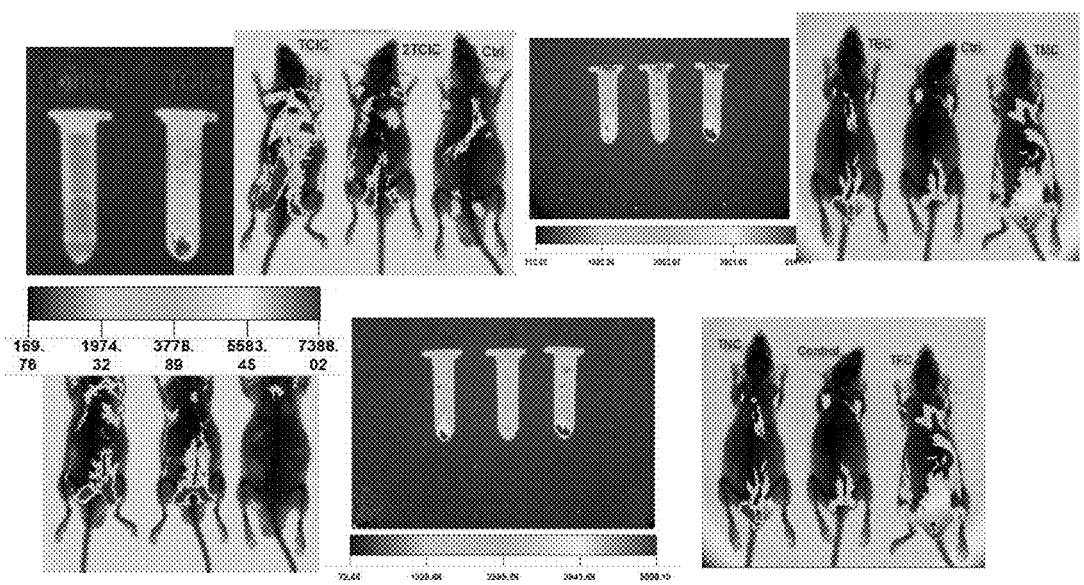
TCIC= compound Ic
Control or Ctrl: Control
TMC= compound Ia
TEC=compound Ib
TNC=compound If
TFC=compound Ie
TBrC=compound Id

CONDENSATION PRODUCT OF THEANINE DERIVATIVE AND CARBOXYLIC ACID COUMARIN DERIVATIVE, ITS INTERMEDIATE, PREPARATION METHOD AND USE THEREOF

CROSS-REFERENCE

This application claims priority under 35 U.S.C. §371 to Patent Cooperation Treaty application PCT/CN2013/084146, filed Sep. 25, 2013, which claims the benefit of Chinese patent application no. 201210363366.6, filed Sep. 27, 2012; Chinese patent application no. 201210363367.0, filed Sep. 27, 2012; Chinese patent application no. 201210363369.X, filed Sep. 27, 2012; Chinese patent application no. 201210363378.9, filed Sep. 27, 2012; Chinese patent application no. 201210515826.2, filed Dec. 6, 2012; Chinese patent application no. 201210515827.7, filed Dec. 6, 2012; and Chinese patent application no. 201310030234.6, filed Jan. 28, 2013; the entire contents of which are incorporated herein by reference.

FIELD OF THE INVENTION

The present invention relates to medical technology, particularly a compound as represented by formula (I), which is a condensation product of a theanine derivative and a carboxylic acid coumarin derivative, compounds as represented by formula (II) and formula (III), both of which are intermediates of the condensation product, a method for preparing these compounds, a pharmaceutical composition comprising the compounds, and use thereof in preparing a medicament for prevention and treatment of tumors, inflammation, cardiovascular disease, immune deficiency diseases and the like.

BACKGROUND OF THE INVENTION

Abnormal growth, invasion and metastasis of malignant tumors, such as human lung cancer, breast cancer, colorectal cancer, prostate cancer, liver cancer, pancreatic cancer, lymphoma, melanoma and the like, are important causes of death of tens of thousands of patients every year. The incidence of the malignant tumors is also kept at a certain level, and the malignant tumors have become major diseases that seriously endanger human health. Due to the clinical toxic and side effects of chemotherapy and radiotherapy, the use of these therapies for effective prevention and treatment of the diseases has been limited. Theanine (also known as γ-glutamylethylamide) is a characteristic amino acid indicating the quality of tea. Because theanine has no toxic and side effects as a food component, it is widely used in food industry as a food additive with its amount unlimited. Studies showed that theanine could increase the concentration of an anti-cancer medicament in the tumor and treated human ovarian cancer in a synergistic manner (Sadzuki et al, Toxicol Lett 123: 159-67, 2001). Our previous experiments proved that theanine had the inhibitory effects on liver cancer and lung cancer (Liu, et al, Cytotechnology 59: 211-217, 2009; Zhang et al. Biosci Biotechnol Biochem 2002, 66 (4): 711-6.). In the invention, a novel condensation product of a theanine derivative and a carboxylic acid coumarin derivative, and an intermediate of the condensation product are formed from theanine by chemical method, and the anti-tumor activity of the compounds exceeds that of the anti-cancer medicaments and the theanine.

Histone methyltransferase EZH2 inhibitor and histone deacetylase (HDAC) inhibitor, such as SAHA (suberoylanilide hydroxamic acid), valproic acid, sodium butyrate and the like have been subjected to phase I or phase II clinical tests for blood and solid tumors in the U.S., EZH2 and HDAC are over expressed in a variety of human cancers, including breast cancer, lung cancer, prostate cancer, leukemia, pancreatic cancer, cervical cancer, intestinal cancer, liver cancer and other malignant tumors. A large number of studies on EZH2 and HDAC as targets of anti-cancer medicaments have been carried out in the U.S., and these EZH2 inhibitors and HDAC inhibitors are widely used in the treatment of various tumors and are considered as potential novel anti-cancer medicaments with good application prospects (Yamaguchi et al., Cancer Sci., 10: 355-62, 2010; Denis, et al., Clin Exp Metastasis 25: 183-189, 2008; Kelly et al., Nat Clin Pract Oncol 2: 150-157, 2005; Martinez-Iglesias et al., Clin Transl Oncol. 10: 395-8, 2008).

A nucleoprotein factor NF-κB is considered as a protein factor promoting a variety of tumors, inflammation, cardiovascular diseases, immune deficiency, and other diseases, and is becoming an important target for prevention and treatment of the diseases (Ishii et al., J Clin Biochem Nutr 50: 91-105, 2012).

The high level of receptors such as VEGFR, EGFR, c-Met, and ER-alpha, and abnormal over expression of protein factors such as K-Ras, H-Ras, Akt, Cyclin D1, MMP-9, MMP-2, Dvl-1, Dvl-2, Dvl-3, β-catenin and Bcl-2 which are associated with signal transduction of tumor, are related to occurrence and progression of a variety of tumors, whereas the increase of the level of tumor suppressor proteins p53, p21, E-cadherin, Caspase3, Bax and cytochrome C shows the inhibition of the growth, invasion and (or) metastasis of a variety of cancer cells (Cengel, et al., Neoplasia 9: 341-8, 2007; Huang et al., Biochem Pharmacol 77: 794-803, 2009; Prasad et al, Oncology. 73: 112-7, 2007). Thus, these cancer-related factors become potential important target for prevention and treatment of cancers, and the compounds which can effectively affect the expressive level and activity of these protein factors have broad application prospects in prevention and treatment of the cancers.

The compound as represented by formula (I), which is a condensation product of a theanine derivative and a carboxylic acid coumarin derivative, and an intermediate thereof as represented by formula (II) and formula (III), all of which are provided by the invention, can significantly affect the level and activity of the above mentioned protein factors, and thus have broad prospects in the preparation of inhibitors for prevention and treatment of tumors, inflammation, cardiovascular diseases, immune deficiency diseases and other diseases.

SUMMARY OF THE INVENTION

One object of the present invention is to provide a compound as represented by formula (I), and intermediates thereof as represented by formula (II) and formula (III):

Formula (I)

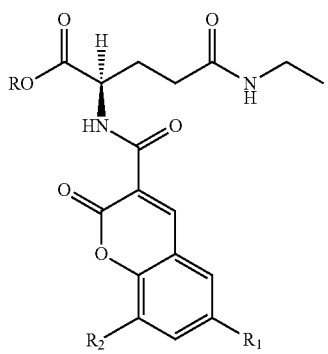

wherein,

| (Ia) | R=CH₃ | R₁=H | R₂=H |
|---|---|---|---|
| (Ib) | R=CH₂CH₃ | R₁=H | R₂=H |
| (Ic) | R=CH₂CH₃ | R₁=Cl | R₂=H |
| (Id) | R=CH₂CH₃ | R₁=Br | R₂=H |
| (Ie) | R=CH₂CH₃ | R₁=F | R₂=H |
| (If) | R=CH₂CH₃ | R₁=NO₂ | R₂=H |
| (Ig) | R=CH₂CH₃ | R₁=Cl | R₂=Cl |
| (Ih) | R=CH₂CH₃ | R₁=Br | R₂=Br |
| (Ii) | R=CH₂CH₃ | R₁=NH₂ | R₂=H |

Formula (II)

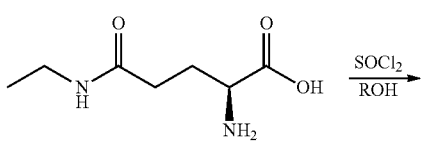

wherein,

| (IIa) | R=CH₃ |
|---|---|
| (IIb) | R=CH₂CH₃ |

Formula (III)

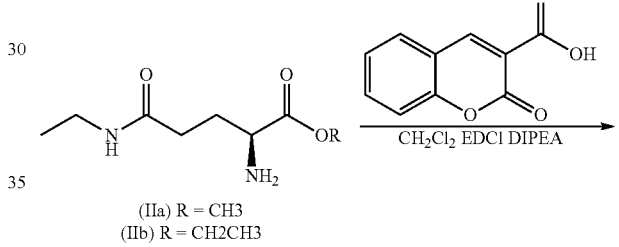

wherein,

| (IIIc) | R₁=Cl | R₂=H |
|---|---|---|
| (IIId) | R₁=Br | R₂=H |
| (IIIe) | R₁=F | R₂=H |
| (IIIf) | R₁=NO₂ | R₂=H |
| (IIIg) | R₁=Cl | R₂=Cl |
| (IIIh) | R₁=Br | R₂=Br |

Another object of the present invention is to provide a method for preparing the compound of the invention:

1) the method for preparing the compounds Ia-Ib and IIa-IIb as described above,

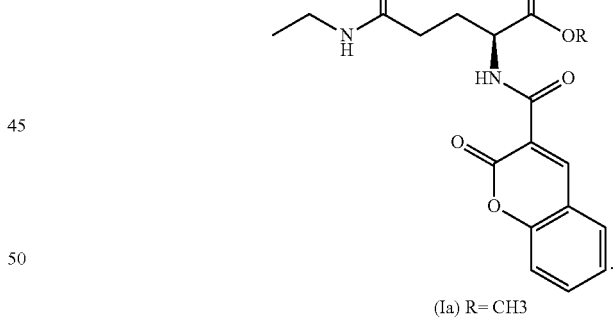

2) the method for preparing the compounds Ic-Ih and IIIc-IIIh as described above,

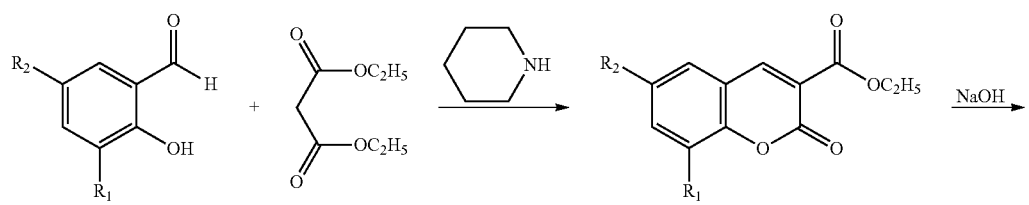

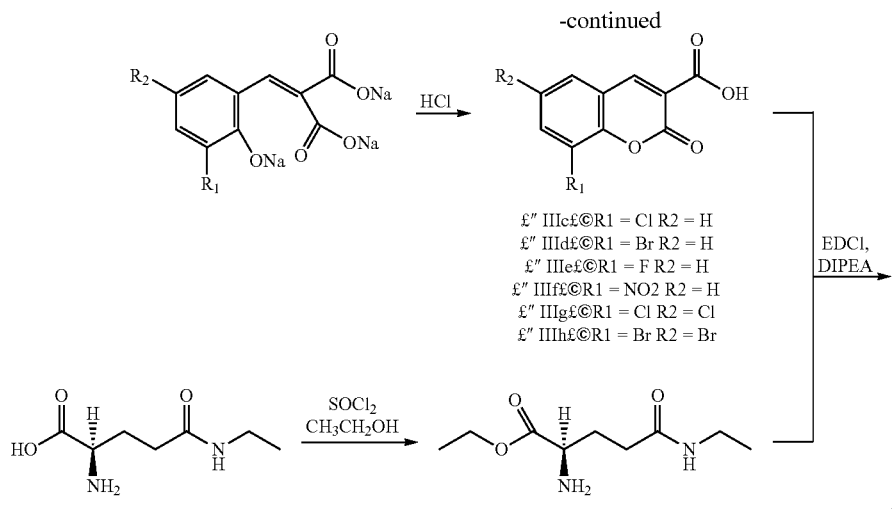

£″ IIIc£©R1 = Cl R2 = H
£″ IIId£©R1 = Br R2 = H
£″ IIIe£©R1 = F R2 = H
£″ IIIf£©R1 = NO2 R2 = H
£″ IIIg£©R1 = Cl R2 = Cl
£″ IIIh£©R1 = Br R2 = Br

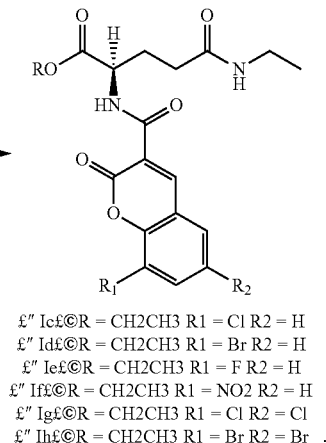

£″ Ic£©R = CH2CH3 R1 = Cl R2 = H
£″ Id£©R = CH2CH3 R1 = Br R2 = H
£″ Ie£©R = CH2CH3 R1 = F R2 = H
£″ If£©R = CH2CH3 R1 = NO2 R2 = H
£″ Ig£©R = CH2CH3 R1 = Cl R2 = Cl
£″ Ih£©R = CH2CH3 R1 = Br R2 = Br .

3) the method for preparing the compound Ii as described above: the compound Ii can be easily obtained by reducing the compound If under a reducing condition.

Another object of the present invention is to provide a pharmaceutical composition comprising the compound of the invention, wherein the pharmaceutical composition comprises at least one compound of the invention and optionally, a pharmaceutical acceptable excipient.

Another object of the present invention is to provide a use of the compounds of the invention, or the compound as represented by formula (IIIa), or the pharmaceutical composition comprising the compound of the invention or the compound as represented by formula (IIIa) in the preparation of a medicament, in particular a medicament for prevention and treatment of human liver cancer, breast cancer, lung cancer, colorectal cancer, prostate cancer, pancreatic cancer, lymphoma, melanoma, and other tumors. Accordingly, the invention provides a method for prevention and treatment of human liver cancer, breast cancer, lung cancer, colorectal cancer, prostate cancer, pancreatic cancer, lymphoma, melanoma and other tumors, including administering to a patient to be treated a therapeutically effective amount of at least one compound of the invention, or the compound as represented by formula (IIIa), or the pharmaceutical composition comprising the compound of the invention or the compound as represented by formula (IIIa):

Formula (IIIa)

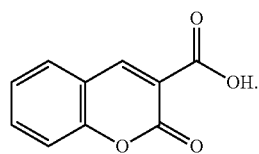

The invention further relates to the compound of the invention, or the compound as represented by formula (IIIa), or the pharmaceutical composition comprising the compound of the invention or the compound as represented by formula (IIIa) for prevention and treatment of human liver cancer, breast cancer, lung cancer, colorectal cancer, prostate cancer, pancreatic cancer, lymphoma, melanoma, and other tumors.

Another object of the present invention is to provide a use of the compound of the invention, or the compound as represented by formula (IIIa), or the pharmaceutical composition comprising the compound of the invention or the compound as represented by formula (IIIa) in the preparation of a histone methyltransferase EZH2 inhibitor, in the preparation of a histone deacetylase (HDAC) inhibitor, in the preparation of an inhibitor for NF-κB, which is the factor related with promotion of tumors, inflammation, cardiovascular diseases, immune deficiency, and other diseases, in the preparation of an inhibitor for factors including VEGFR, EGFR, c-Met, ER-alpha, K-Ras, H-Ras, Akt, Cyclin D1, MMP-9, MMP-2, Dvl-1, Dvl-2, Dvl-3, β-catenin and Bcl-2, which are related with tumors, inflammation, cardiovascular diseases, immune deficiency and other diseases, and in the preparation of an activator for increasing Bax, p53, p21, E-cadherin, Caspase3, and cytoplasma/mitochondrial cytochrome C ratio. Accordingly, the invention provides a method for inhibiting histone methyltransferase EZH2, a method for inhibiting histone deacetylase (HDAC), a method for inhibiting NF-κB, which is the factor related with promotion of tumors, inflammation, cardiovascular diseases, immune deficiency, and other diseases, a method for inhibiting factors including VEGFR, EGFR, c-Met, ER-alpha, K-Ras, H-Ras, Akt, Cyclin D1, MMP-9, MMP-2, Dvl-1, Dvl-2, Dvl-3, β-catenin, and Bcl-2, which are related with tumors, inflammation, cardiovascular diseases, immune deficiency, and other diseases, and a method for increasing Bax, p53, p21, E-cadherin, Caspase3, and cytoplasma/mitochondrial cytochrome C ratio.

The present invention further relates to the compound of the invention for inhibiting histone methyltransferase EZH2, for inhibiting histone deacetylase (HDAC), for inhibiting NF-κB, which is the factor related with promotion of tumors, inflammation, cardiovascular diseases, immune deficiency, and other diseases, for inhibiting factors including VEGFR, EGFR, c-Met, ER-alpha, K-Ras, H-Ras, Akt, Cyclin D1, MMP-9, MMP-2, Dvl-1, Dvl-2, Dvl-3, β-catenin, and Bcl-2, which are related with tumors, inflammation, cardiovascular diseases, immune deficiency, and other diseases, and for increasing Bax, p53, p21, E-cadherin, Caspase3, and cytoplasma/mitochondrial cytochrome C ratio.

BRIEF DESCRIPTION OF THE DRAWINGS

FIG. 1 provides fluorescent images detected in vivo and in vitro of the compounds Ia-Ih as obtained in embodiments 1-7.

DETAILED DESCRIPTION OF THE EMBODIMENTS

One object of the invention is to provide a compound as represented by formula (I), and intermediates thereof as represented by formula (II) and formula (III):

Formula (I)

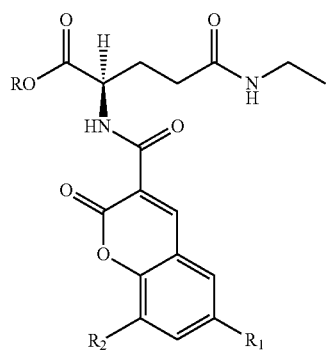

wherein,

| (Ia) | R=CH$_3$ | R$_1$=H | R$_2$=H |
|---|---|---|---|
| (Ib) | R=CH$_2$CH$_3$ | R$_1$=H | R$_2$=H |
| (Ic) | R=CH$_2$CH$_3$ | R$_1$=Cl | R$_2$=H |
| (Id) | R=CH$_2$CH$_3$ | R$_1$=Br | R$_2$=H |
| (Ie) | R=CH$_2$CH$_3$ | R$_1$=F | R$_2$=H |
| (If) | R=CH$_2$CH$_3$ | R$_1$=NO$_2$ | R$_2$=H |
| (Ig) | R=CH$_2$CH$_3$ | R$_1$=Cl | R$_2$=Cl |
| (Ih) | R=CH$_2$CH$_3$ | R$_1$=Br | R$_2$=Br |
| (Ii) | R=CH$_2$CH$_3$ | R$_1$=NH$_2$ | R$_2$=H |

Formula (II)

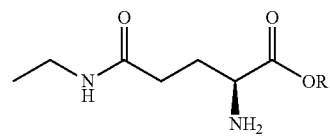

wherein,

| (IIa) | R=CH$_3$ |
|---|---|
| (IIb) | R=CH$_2$CH$_3$ |

Formula (III)

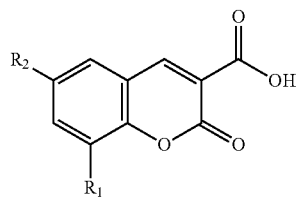

wherein,

| (IIIc) | R$_1$=Cl | R$_2$=H |
|---|---|---|
| (IIId) | R$_1$=Br | R$_2$=H |
| (IIIe) | R$_1$=F | R$_2$=H |
| (IIIf) | R$_1$=NO$_2$ | R$_2$=H |
| (IIIg) | R$_1$=Cl | R$_2$=Cl |
| (IIIh) | R$_1$=Br | R$_2$=Br |

Specifically, the name of the compound Ia is methyl 5-ethylamino-5-oxo-2-(2-oxo-2H-benzopyran-3-carboxamido)pentanoate, referred to as TMC, and the compound Ia has the chemical structural formula as shown below:

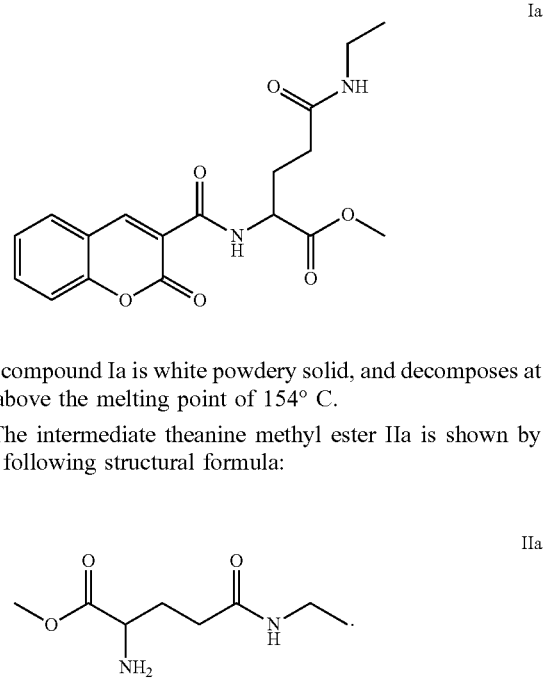

the compound Ia is white powdery solid, and decomposes at or above the melting point of 154° C.

The intermediate theanine methyl ester IIa is shown by the following structural formula:

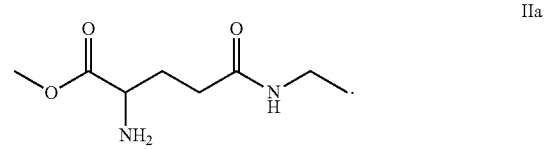

The name of the compound Ib is ethyl 5-ethylamino-5-oxo-2-(2-oxo-2H-benzopyran-3-carboxamido)pentanoate, referred to as TEC, and the compound Ib has the chemical structural formula as shown below:

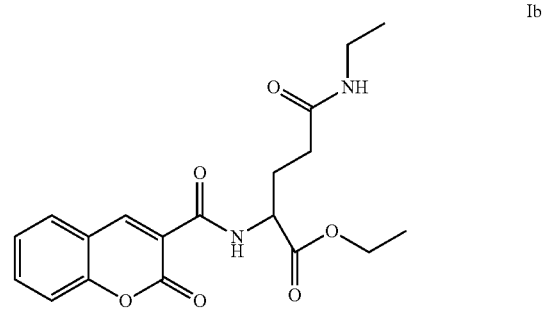 [SMILES: CCNC(=O)CCC(NC(=O)c1cc2ccccc2oc1=O)C(=O)OCC]

the compound Ib is white powdery solid and decomposes at or above the melting point of 180° C.

The intermediate theanine ethyl ester IIb is shown by the following structural formula:

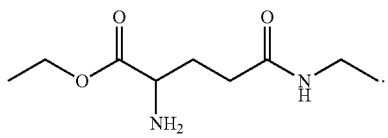

IIb

The name of the compound Ic is (R)-2-(6-Cl-2-oxo-2H-benzopyran-3-carboxamido)-5-ethylamino-5-oxo-pentanoic acid ethyl ester, referred to as TCIC, and the compound Ic has the chemical structural formula as shown below:

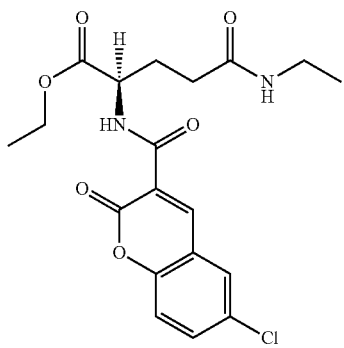

Ic the compound is light yellow powdery solid and decomposes at or above the melting point of 242° C.

The intermediate 6-chlorocoumarin-3-carboxylic acid is shown by the following formula:

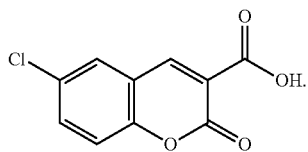

IIIc

The name of the compound Id is (R)-2-(6-Br-2-oxo-2H-benzopyran-3-carboxamido)-5-ethylamino-5-oxo-pentanoic acid ethyl ester, referred to as TBrC, and the compound Id has the chemical structural formula as shown below:

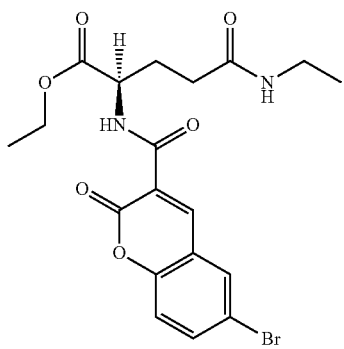

Id the compound is light yellow powdery solid and decomposes at or above the melting point of 211° C.

The intermediate 6-bromocoumarin-3-carboxylic acid IIId is shown by the following formula:

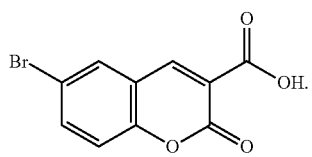

IIId

The name of the compound Ie is (R)-2-(6-F-2-oxo-2H-benzopyran-3-carboxamido)-5-ethylamino-5-oxo-pentanoic acid ethyl ester, referred to as TFC, and the compound Ie has the chemical structural formula as shown by the following formula:

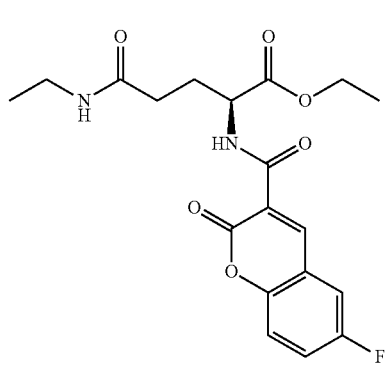

Ie the compound is light yellow powdery solid and decomposes at or above the melting point of 65° C.

The intermediate 6-fluorocoumarin-3-carboxylic acid IIIe is shown below:

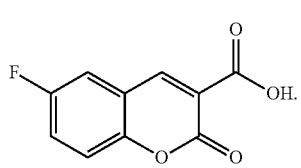

IIIe

The name of the compound If is (R)-2-(6-nitro-2-oxo-2H-benzopyran-3-carboxamido)-5-ethylamino-5-oxo-pentanoic acid ethyl ester, referred to as TNC, and the compound If has the chemical structural formula as shown below:

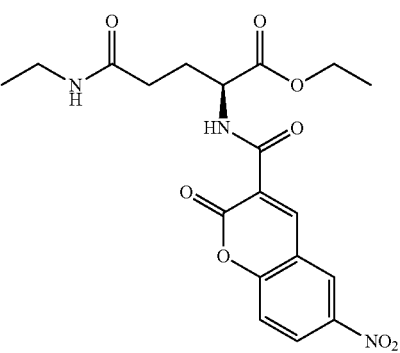

If the compound is light yellow powdery solid and decomposes at or above the melting point of 300° C.

The intermediate 6-nitrocoumarin-3-carboxylic acid IIIf is shown below:

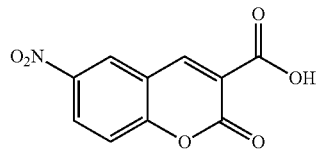

IIIf

The name of the compound Ig is (R)-2-(6,8-dichloro-2-oxo-2H-benzopyran-3-carboxamido)-5-ethylamino-5-oxopentanoic ethyl ester, referred to as DTClC, and the compound Ig has the chemical structural formula as shown below:

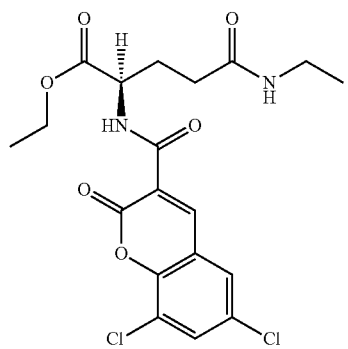

Ig

The name of the compound Ih is (R)-2-(6,8-dibromo-2-oxo-2H-benzopyran-3-carboxamido)-5-ethylamino-5-oxopentanoic ethyl ester, referred to as DTBrC, and the compound Ih has the chemical structural formula as shown below:

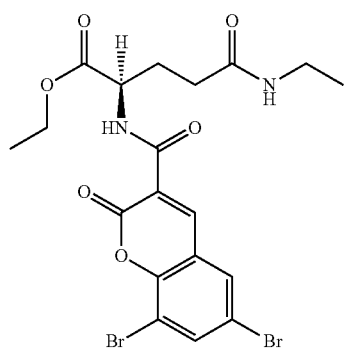

Ih both of the compounds Ig and Ih are light yellow powdery solid and decompose at or above the melting points of 136° C. and 121° C. respectively.

The intermediate 6,8-dichloro-coumarin-3-carboxylic acid IIIg is shown by the following formula:

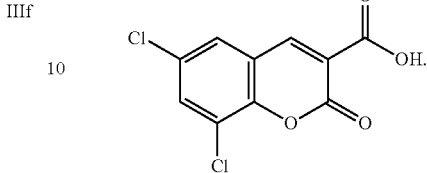

IIIg

The intermediate 6,8-dibromo-coumarin-3-carboxylic acid IIIh is shown by the following formula:

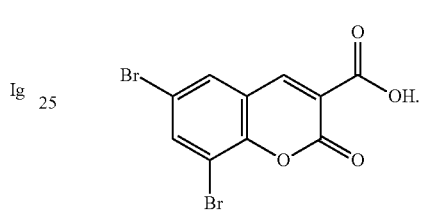

IIIh

The name of the compound Ii is (R)-2-(6-amino-2-oxo-2H-benzopyran-3-carboxamido)-5-ethylamino-5-oxo-pentanoic acid ethyl ester, and the compound Ii has the chemical structural formula as shown below:

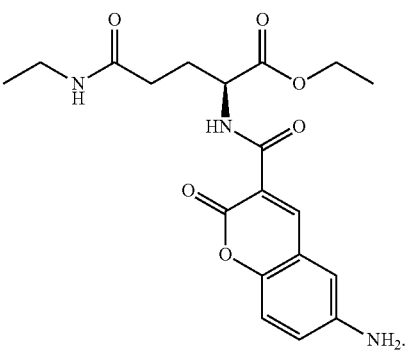

Ii

Another object of the present invention is to provide a method for preparing the compounds of the invention:

1) the method for preparing the compounds Ia-Ib and IIa-IIb as described above,

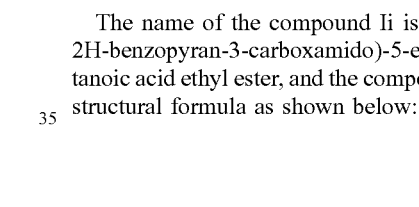

Theanine

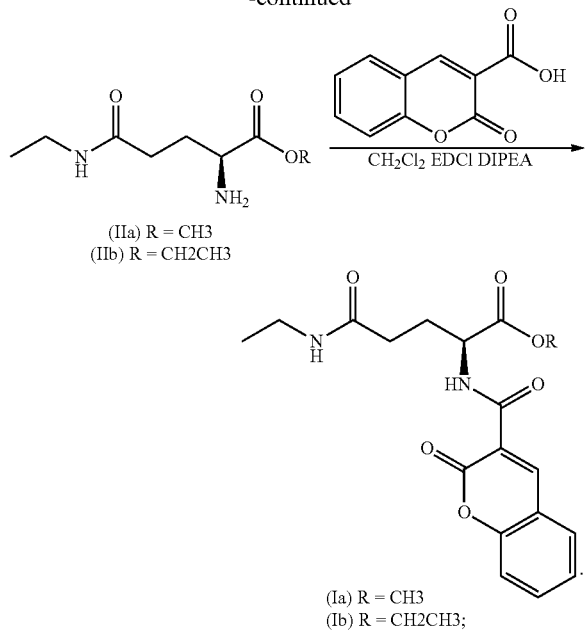

(IIa) R = CH3
(IIb) R = CH2CH3

(Ia) R = CH3
(Ib) R = CH2CH3;

2) the method for preparing the compounds Ic-Ih and IIIc-IIIh as described above,

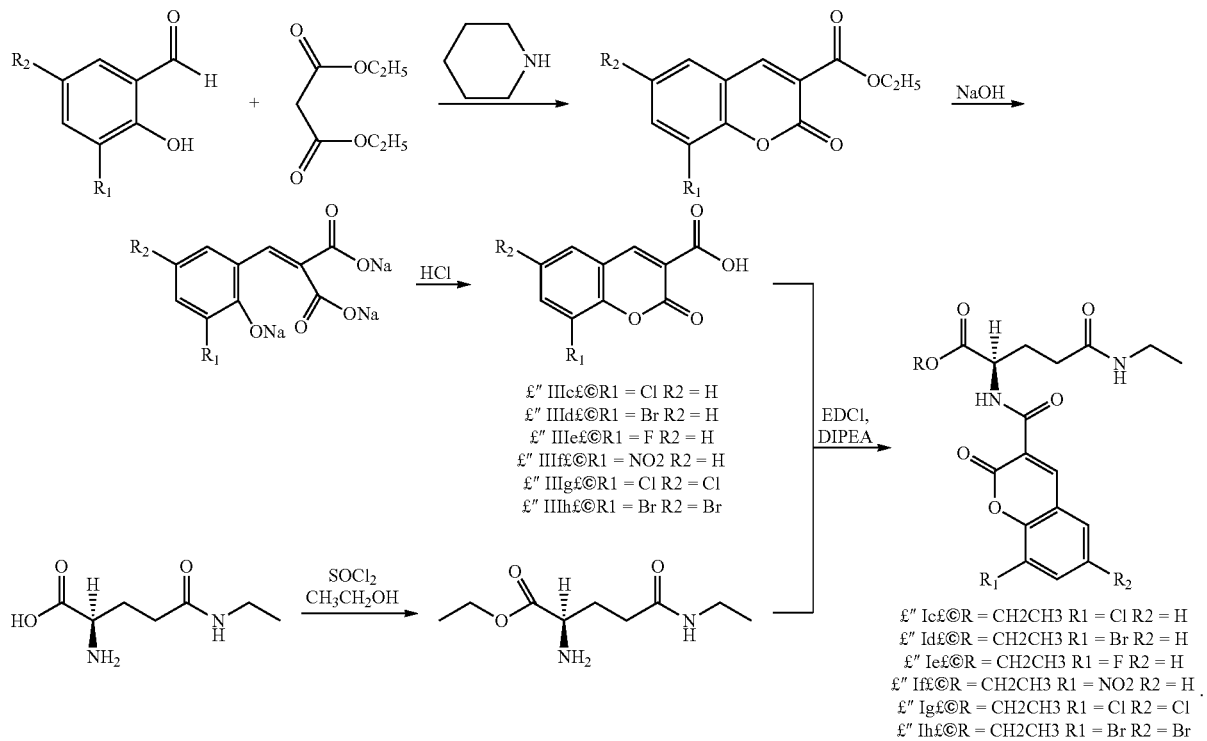

£″ IIIc£©R1 = Cl R2 = H
£″ IIId£©R1 = Br R2 = H
£″ IIIe£©R1 = F R2 = H
£″ IIIf£©R1 = NO2 R2 = H
£″ IIIg£©R1 = Cl R2 = Cl
£″ IIIh£©R1 = Br R2 = Br

£″ Ic£©R = CH2CH3 R1 = Cl R2 = H
£″ Id£©R = CH2CH3 R1 = Br R2 = H
£″ Ie£©R = CH2CH3 R1 = F R2 = H
£″ If£©R = CH2CH3 R1 = NO2 R2 = H
£″ Ig£©R = CH2CH3 R1 = Cl R2 = Cl
£″ Ih£©R = CH2CH3 R1 = Br R2 = Br 3) the method for preparing the compound Ii: the compound Ii can be easily obtained by reducing the compound If under a reducing condition.

The invention further provides a pharmaceutical composition comprising the compound of the invention. The invention provides such a pharmaceutical composition, which comprises at least one compound of the invention and optionally, a pharmaceutically acceptable excipient.

As used herein, unless otherwise indicated, the term 'prodrug' refers to a derivative which can be hydrolyzed, oxidized or subjected to other reactions under biological conditions (in vitro or in vivo) to provide the compound of the invention. The prodrug is converted to active form through the reactions under biological conditions, or has activity in its unreacted forms. Generally, the prodrug can be prepared by the known methods, such as the methods described in 1 Burger's Medicinal Chemistry and Drug Discovery (1995) 172-178, 949-982 (Manfred E. Wolff ed., 5th ed).

The prodrug can be prepared by chemical modification through the following ways: the prodrug of the compound of the invention can be prepared by connecting monosaccharides for example glucose, or vitamin C, propanediol and other carbohydrate and alcohol compounds to 7-hydroxyl group of the coumarin derivative or to the amino group, alkyl group and carbonyl group of the theanine derivative as shown below, and the glucosidic bond, ester bond, amide bonds and the like formed by such modification can be hydrolyzed in vivo so that the prodrug can be converted to the active compound of the invention to exert the bioactivity.

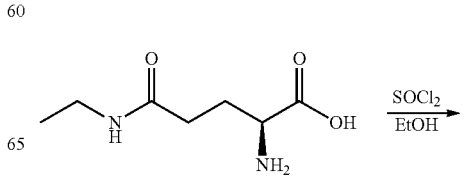

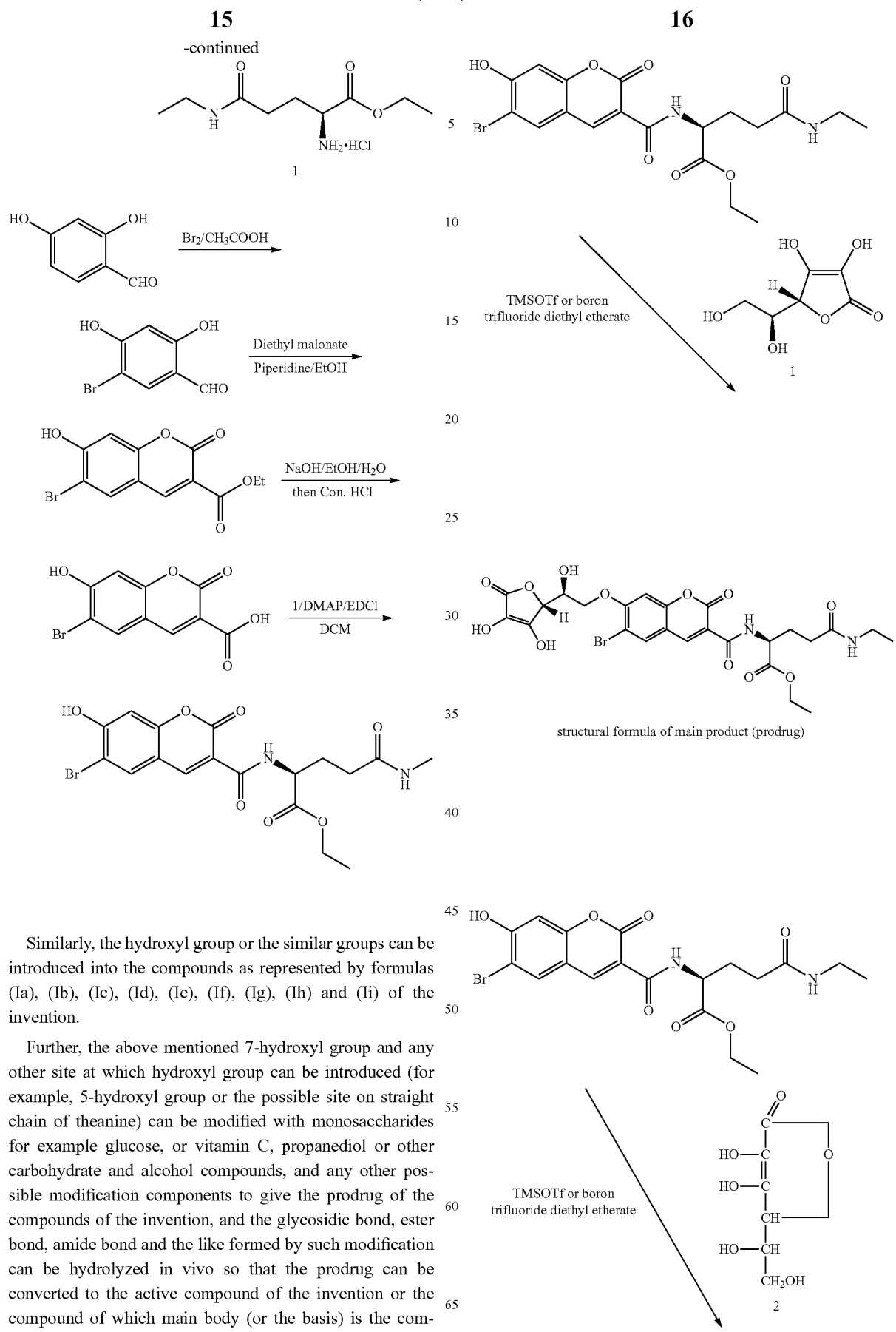

Similarly, the hydroxyl group or the similar groups can be introduced into the compounds as represented by formulas (Ia), (Ib), (Ic), (Id), (Ie), (If), (Ig), (Ih) and (Ii) of the invention.

Further, the above mentioned 7-hydroxyl group and any other site at which hydroxyl group can be introduced (for example, 5-hydroxyl group or the possible site on straight chain of theanine) can be modified with monosaccharides for example glucose, or vitamin C, propanediol or other carbohydrate and alcohol compounds, and any other possible modification components to give the prodrug of the compounds of the invention, and the glycosidic bond, ester bond, amide bond and the like formed by such modification can be hydrolyzed in vivo so that the prodrug can be converted to the active compound of the invention or the compound of which main body (or the basis) is the compound of the invention to exert the bioactivity.

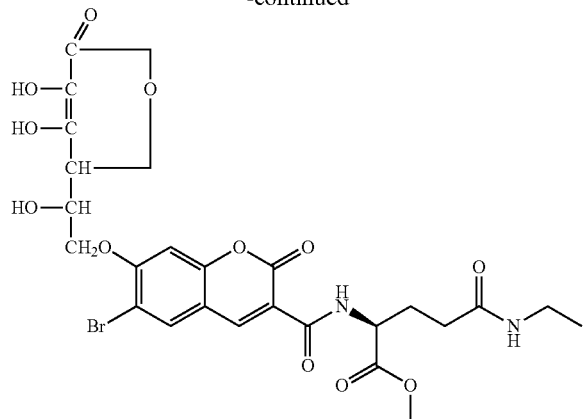

structural formula of main product (prodrug)

The method for preparing various pharmaceutical compositions comprising a certain amount of active component is known or obvious to those skilled in the art according to the disclosure of the invention. As described in REMINGTON'S PHARMACEUTICAL SCIENCES, Martin, E W, ed., Mack Publishing Company, 19th ed. (1995), the method for preparing the pharmaceutical composition comprises the step of incorporating an appropriate pharmaceutical excipient, a carrier, a diluent and the like.

The known method for preparing the pharmaceutical preparation of the invention comprises a conventional mixing, dissolution or lyophilizing method. The compound of the invention can be made into the pharmaceutical composition and administered to a patient in various ways which are suitable for the selected application mode, such as oral or parenteral administration (through intravenous, intramuscular, topical or subcutaneous ways, spraying in nasal cavity and other parts, tablet pasting and the like).

Thus, the compound of the invention combined with the pharmaceutical acceptable carrier (such as inert diluent or assimilable and edible carrier) can be systematically administrated, such as oral administration. They can be sealed in hard or soft-shelled gelatin capsules or can be pressed into tablets. For the oral administration, the active compounds can be combined with one or more excipients, and can be used in the forms of deglutible tablets, buccal tablets, troches, capsules, elixirs, suspensions, syrups, wafers and the like. Such composition or preparation should contain at least 0.1% of the active compound. The proportion in the composition or preparation can be changed in the range of about 1% to about 99% of the weight of the given unit dosage form. In such a therapeutically useful composition, the amount of the active compound should to be sufficient to achieve an effective dose.

Tablets, troches, pills, capsules and the like can also comprise binders, such as tragacanth, acacia, corn starch or gelatin; excipients, such as calcium hydrogen phosphate; disintegrants, such as corn starch, potato starch, alginic acid and the like; lubricants, such as magnesium stearate; and sweeteners, such as sucrose, fructose, lactose or aspartame; or flavoring agents, such as peppermint, wintergreen oil or cherry flavor. When the unit dosage form is the capsule, in addition to the above materials, a liquid carrier, such as vegetable oil or polyethylene glycol can be also included. Other various materials can exist, as coatings or other physical forms that can change solid unit dosage form in other ways. For example, tablets, pills or capsules can be coated with gelatin, wax, shellac or sugar and the like. Syrups or elixirs can comprise the active compound, sucrose or fructose as the sweetener, methyl paraben or propyl paraben as a preservative, a dye and a flavoring agent (such as cherry flavor or orange flavor). Of course, any material for preparing any unit dosage form should be pharmaceutically acceptable, and basically non-toxic in the application amount. In addition, the active compound can be blended into a sustained-release preparation and a sustained-release device.

The active compound can be intravenously or intraperitoneally administered by infusion or injection. A water solution of the active compound or a salt thereof can be prepared and be optionally mixed with a non-toxic surfactant. Dispersants in glycerol, liquid polyethylene glycol, glycerol triacetate and the mixture thereof, as well as in oil can also be prepared. Under common storage and using conditions, these preparations comprise the preservative for preventing the growth of microbes.

The pharmaceutical dosage forms which are suitable for injection or infusion can comprise sterile water solutions or the dispersants or sterile powder comprising active components (optionally packaged in liposomes), which are suitable for instant preparations of the sterile injectable or infusible solutions or the dispersants. In all cases, the final dosage forms must be sterile, liquid and stable under processing and storage conditions. The liquid carrier can be a solvent or a liquid dispersion medium, such as water, ethanol, polyols (such as glycerol, propanediol, liquid polyethylene glycol and the like), vegetable oil, non-toxic glycerides and suitable mixtures thereof. The appropriate flowability can be maintained, for example, by forming the liposomes, maintaining the required particle size in the presence of the dispersant, or using the surfactant. The various antibacterial and antifungal agents (such as parabens, chlorobutanol, phenol, sorbic acid, thimerosal and the like) can be used to prevent the microbes. In many cases, an isotonic agent, such as sugar, a buffering agent or sodium chloride are preferably included. The delayed absorption of the injectable composition can be achieved by using a composition of absorption delaying agent (such as aluminum monostearate and gelatin).

The sterile injectable solution can be prepared by combining the required amount of the active compound in an appropriate solvent with various components listed above and then performing filtration and sterilization. When preparing the sterile powder from the sterile injection solution, the preferable preparation method is vacuum drying and freeze-drying technique, which would produce the powder of the active component and any other components required in the previous sterile filtered solution.

The useful solid carriers include crushed solids (such as talcum, clay, microcrystalline cellulose, silicon dioxide, aluminum oxide and the like). The useful liquid carrier includes water, ethanol, ethylene glycol or a water-ethanol/ethylene glycol mixture, and the compound of the invention can be dissolved or dispersed in the liquid carrier at an effective content under the assistance of non-toxic surfactant. Adjuvants (such as flavors) and additional antimicrobial agents can be added for optimizing the properties for given use.

Thickeners (such as synthetic polymers, fatty acids, fatty acid salts and esters, fatty alcohols, modified celluloses or modified inorganic materials) together with the liquid carriers can also be used to form spreadable pastes, gels, ointments, soaps and the like, which can be directly applied on the skin of users.

The required amount of the compound for treatment depends on not only the selected specific salt, but also the application modes, the nature of the disease to be treated and the age and state of the patient, and finally depends on the decision of an on-site physician or a clinician.

The above mentioned preparation can exist in an unit dosage form, which is a physical dispersion unit containing unit dose and is suitable for delivery to human bodies and other mammals. The unit dosage form can be a capsule or a tablet, or a plurality of capsules or tablets. According to the specific treatment involved, the amount of the unit dose of the active component can be changed or adjusted in the range of about 1 mg to about 2000 mg or more.

In addition, the invention further comprises applications of various new pharmaceutical dosage forms, such as emulsive liposomes, microspheres and nanospheres, such as medicaments prepared by using microparticle dispersion systems, including polymeric micelles, nanoemulsions, submicroemuls, microcapsules, microspheres, liposomes, niosomes (also known as non-ionic surfactant vesicles) and the like.

The invention further provides an use of the compound of the invention or the compound as represented by formula (IIIa), or the pharmaceutical composition comprising the compound of the invention or the compound as represented by formula (IIIa) in the preparation of a medicament, in particular the medicament for prevention and treatment of human liver cancer, breast cancer, pancreatic cancer, lung cancer, colorectal cancer, prostate cancer, lymphoma, melanoma and other tumors. Accordingly, the invention provides a method for prevention and treatment of human liver cancer, breast cancer, pancreatic cancer, lung cancer, colorectal cancer, prostate cancer, lymphoma, melanoma and other tumors, including administering to a patient to be treated a therapeutically effective amount of at least one compound of the invention, or the compound as represented by formula (IIIa), or the composition comprising the compound of the invention or the compound as represented by formula (IIIa).

The invention further relates to the compound of the invention, or the compound as represented by formula (IIIa), or the composition comprising the compound of the invention or the compound as represented by formula (IIIa) for prevention and treatment of human liver cancer, lung cancer, breast cancer, colorectal cancer, prostate cancer, pancreatic cancer, lymphoma, melanoma and other tumors.

Another object of the invention is to provide a use of the compound of the invention, or the compound as represented by formula (IIIa), or the pharmaceutical composition comprising the compound of the invention or the compound as represented by formula (IIIa) in the preparation of a histone methyltransferase EZH2 inhibitor, in the preparation of a histone deacetylase (HDAC) inhibitor, in the preparation of an inhibitor for NF-κB, which is the factor related with promotion of tumors, inflammation, cardiovascular diseases, immune deficiency and other diseases, in the preparation of an inhibitor for factors including VEGFR, EGFR, c-Met, ER-alpha, K-Ras, H-Ras, Akt, Cyclin D1, MMP-9, MMP-2, Dvl-1, Dvl-2, Dvl-3, β-catenin and Bcl-2/Bax which are related with tumors, inflammation, cardiovascular diseases, immune deficiency, and other diseases, in the preparation of an activator for increasing p53, p21, E-cadherin, Caspase3 and cytoplasma/mitochondrial cytochrome C ratio. Accordingly, the invention provides a method for inhibiting histone methyltransferase EZH2, a method for inhibiting histone deacetylase (HDAC), a method for inhibiting NF-κB which is the factor related with promotion of tumors, inflammation, cardiovascular diseases, immune deficiency and other diseases, a method for inhibiting factors including VEGFR, EGFR, c-Met, ER-alpha, K-Ras, H-Ras, Akt, Cyclin D1, β-catenin, MMP-9, MMP-2, Dvl-1, Dvl-2, Dvl-3, and Bcl-2 which are related with tumors, inflammation, cardiovascular diseases, immune deficiency, and other diseases, and a method for increasing Bax, p53, p21, E-cadherin, Caspase3 and cytoplasma/mitochondrial cytochrome C ratio.

The invention further relates to the compound of the invention for inhibiting histone methyltransferase EZH2, inhibiting histone deacetylase (HDAC), inhibiting NF-κB which is the factor related with promotion of tumors, inflammation, cardiovascular diseases, immune deficiency and other diseases, inhibiting factors including VEGFR, EGFR, c-Met, ER-alpha, K-Ras, H-Ras, Akt, Cyclin D1, β-catenin, MMP-9, MMP-2, Dvl-1, Dvl-2, Dvl-3 and Bcl-2/Bax which are related with tumors, inflammation, cardiovascular diseases, immune deficiency and other diseases and increasing p53, p21, E-cadherin, Caspase3 and cytoplasma/mitochondrial cytochrome C ratio.

The compounds of the invention can be combined with radiotherapy, chemotherapy, surgery, thermal therapy and the like for treatment of tumors, and can be used in the preparation of a medicament for cooperated with radiotherapy, chemotherapy, surgery, thermal therapy and the like for the treatment of tumors.

The compounds of the invention can effectively kill tumor cells and enhance the effects of radiotherapy and chemotherapeutic medicaments in the treatment of tumors, and the effects of the compound in inhibition of tumors exceeds that of the anti-cancer medicament and theanine; furthermore, the toxic and side effects are greatly reduced, and the compounds have no obvious toxic and side effects.

The tumors include lung cancer, breast cancer, liver cancer, rectal cancer, colon cancer, prostate cancer, gastric cancer, esophageal cancer, brain and neurogenic tumors, laryngeal cancer, leukemia, lymphoma, melanoma, uterine cancer, retinal tumor, ovarian cancer, skin cancer, bronchial cancer, bronchiolar cancer, urethral cancer, kidney cancer, oral cancer, vaginal cancer, bile duct cancer, pancreatic cancer, bladder cancer, nasopharyngeal cancer and other various tumors.

The compounds provided by the invention can integrate the effects of chemotherapy and synergy with radiotherapy, and are novel anti-tumor medicaments with a wider range of applications, better curative effects, smaller toxic and side effects, wider indications and greater potential application value and market benefits.

The compounds and the intermediates thereof obtained according to the invention can be used by intramuscular, subcutaneous, intravenous and intraperitoneal injection or oral administration, and the effects for the treatment of a variety of human cancer cells, animal cancer cells and human cancer xenografts in animal are better than theanine and some clinical anti-cancer medicaments, such as vincristine, daunorubicin, cyclophosphamide, endostar and the like.

The flurorescent property of the compounds and the intermediates thereof obtained according to the invention can be applied through the following ways. About the applications of the fluorescent properties: 1) as a fluorescent label: for all the indications and decorations in the dark, illumination identifier, decorations, toys, stage properties, particular fluorescent signs of daily necessaries, energy-saving lamps, neon lamps, dark clothes, such as clothes, hats, shoes, gloves and backpacks, position logos and safety states of appliances, and the like. 2) as an indicator for changes of environmental conditions, such as an indicator of the environmental changes and the food quality, with the color changing when the ambient pH value, $O_2$, $CO_2$, Na, Ca, $NO_3$, redox state and the like change (such as, when $Ca^{2+}$ is added into a fluorescent probe solution of the compound, the fluorescence intensity of a probe is increased sharply at about 450 nm; and when a coumarin type anionic fluorescent probe is used, such a probe can selectively identify $HSO_3^-$ and the like in the water solution). The compound can also be used for experimental research and application as molecular probes, for example, in the aspect of medical health, when the compound of the invention is used for labeling cells or medicaments or components, the compound can display its positions in cells or in the body, the migration positions of the cells in vivo and the binding targets, such as proteins, enzymes, receptors and the like, thereby realizing the effects of diagnostic prediction and assessment.

In the following embodiments, the invention is further explained. It should be understood that the following embodiments are only used to illustrate the invention rather than defining the scope of the invention.

Chemical raw materials as used in the following embodiments are commercially available or synthesized via the methods well known in the art.

(The temperature involved in the application refers to Celsius temperature).

EMBODIMENTS

Embodiment 1

Preparation of the Compound Ia and the Intermediate IIa Thereof

The general steps of the reaction are as follows:

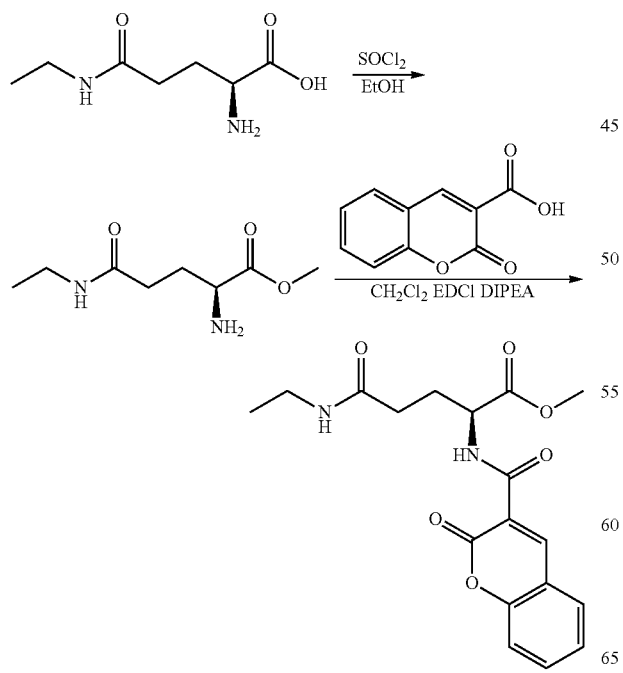

Step 1: Preparation of Theanine Methyl Ester IIa

Theanine was dissolved in methanol in an proportion of 87 g/L (namely, 87 g of theanine was dissolved in one liter of methanol), then sulfonyl chloride was slowly added into the system in an volume ratio of 55 ml, the mixture was stirred at room temperature for 1 h, and the resulting mixture was concentrated under reduced pressure to afford theanine methyl ester IIa.

Step 2: Preparation of TMC Ia 20 g of theanine methyl ester was dissolved in 2 L of anhydrous dichloromethane, 27 g of 3-carboxylic acid coumarin was added, then 0.21 L of DIPEA (diisopropylethylamine) and 76 g of EDCI were added respectively. The resulting mixture was stirred at room temperature for 1 h, then concentrated under reduced pressure to remove the solvent, the residue was purified by column chromatography, and the product of TMC Ia was collected. The product was light yellow powdery solid and decomposed at or above the melting point of 180° C., and the structure characteristics of the compound were as follows:

$^1$H NMR (500 MHz, $CDCl_3$) δ 1.15 (t, 3H, J=7.2 Hz), 2.10-2.17 (m, 1H), 2.28-2.31 (m, 2H), 2.34-2.41 (m, 1H), 3.27-3.33 (m, 2H), 3.78 (s, 3H), 4.78-4.83 (m, 1H), 6.07 (br s, 1H), 7.38-7.43 (m, 2H), 7.67-7.71 (m, 2H), 8.88 (s, 1H), 9.35 (br d, 1H, J=7.6 Hz); $^{13}$C NMR (125 MHz, $CDCl_3$) δ 14.81, 28.72, 32.57, 34.47, 52.29, 52.63, 116.75, 117.93, 118.47, 125.39, 129.89, 134.40, 148.81, 154.57, 161.17, 161.74, 171.22, 171.75; ESI-MS m/z 361 [M+1].

Embodiment 2

Preparation of the Compound Ib and the Intermediate IIb Thereof

The general steps of the reaction are as follows:

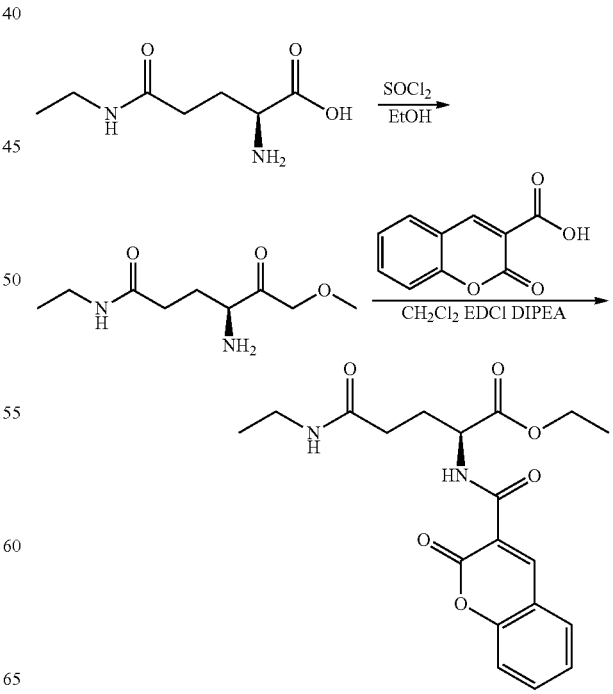

Step 1: Preparation of Theanine Ethyl Ester IIb

Theanine was dissolved in ethanol in an proportion of 87 g/L (namely, 87 g of theanine was dissolved in one liter of methanol), then sulfonyl chloride was slowly added into the system in a volume ratio of 55 ml, the mixture was stirred at room temperature for 1 h, and then the resulting mixture was concentrated under reduced pressure to obtain theanine ethyl ester IIb.

Step 2: Preparation of TEC Ib 20 g of theanine ethyl ester was dissolved in 2 L of anhydrous dichloromethane, 27 g of 3-carboxylic acid coumarin was added, then 0.21 L of DIPEA (diisopropylethylamine) and 76 g of EDCI were added respectively. The mixture was stirred at room temperature for 1 h, then concentrated under reduced pressure to remove the solvent, the residue was purified by column chromatography, and the product of TEC Ib was collected. The product was light yellow powdery solid and decomposed at or above the melting point of 180° C., and the structure characteristics of the compound were as follows:

$^1$H NMR (500 MHz, CDCl$_3$) δ 1.11 (t, 3H, J=7.2 Hz), 1.28 (t, 3H, J=7.1 Hz), 2.17-2.28 (m, 3H), 2.31-2.40 (m, 1H), 3.23-3.28 (m, 2H), 4.10-4.13 (m, 1H), 4.18-4.22 (q, 2H, J=7.1 Hz), 5.61 (br s, 1H), 6.90 (dt, 1H, J=7.5, 0.8 Hz), 6.97 (d, 1H, J=8.2 Hz), 7.28 (dd, 1H, J=7.7, 1.6 Hz), 7.34 (dt, 1H, J=8.5, 1.6 Hz), 8.39 (s, 1H), 12.96 (br s, 1H); $^{13}$C NMR (125 MHz, CDCl$_3$) δ 14.2, 14.8, 29, 32, 34, 61, 70, 117, 118.5, 118.9, 131, 132, 160, 167, 170, 171; ESI-MS m/z 375 [M+1].

Embodiment 3

Preparation of the Compound Ic and the Intermediate IIIc Thereof

The general steps of the reaction are as follows:

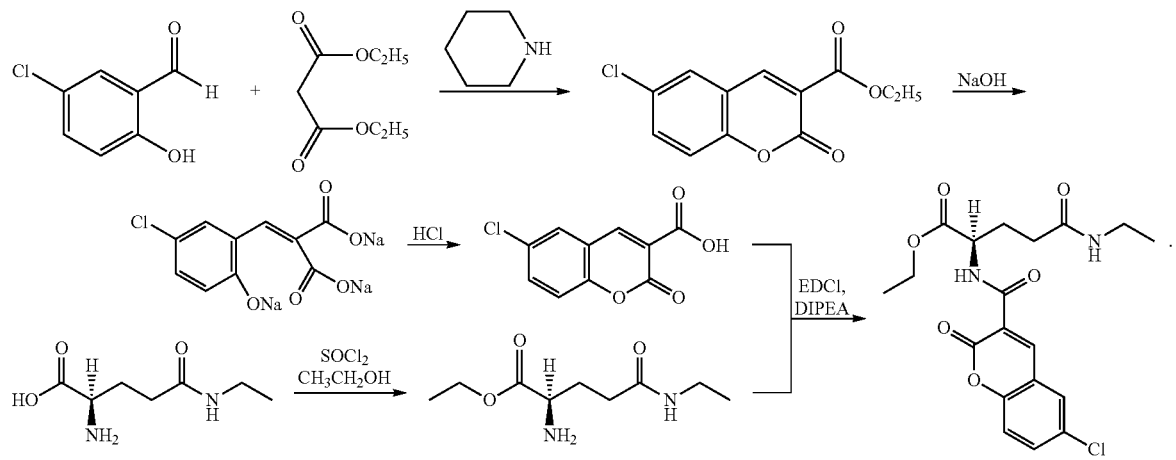

Step 1: Preparation of 6-Chloro-Coumarin-3-Carboxylic Acid IIIc 200 g of 5-chlorosalicylaldehyde, 200 mL of diethyl malonate, 600 mL of anhydrous ethanol, 10 mL of piperidine (10.3 g) and 1 ml of glacial acetic acid were added in sequence; (2) the mixture was stirred and refluxed for 2 h at 80° C. in water bath under anhydrous condition, and cooled; (3) about 600 mL of cold water (0° C.) was added, the mixture was filtered after precipitation of crystals, and the filter cake was washed twice with 100 mL of 50% ethanol which was cooled by ice water (0° C.) to obtain 6-chloro-coumarin-3-carboxylate; (4) 124 g of ethyl 6-chlorocoumarin-3-carboxylate and 100 g of sodium hydroxide were respectively added, then 500 mL of anhydrous ethanol and 500 mL of water were added, and the mixture was heated and refluxed at 80° C. in water bath for about 2 h; and (5) the mixture was immediately placed into an 0° C. ice bath after the reaction, concentrated hydrochloric acid was added to enable the pH value of the system to be 2-3 so as to precipitate solids from the system, the mixture was cooled by the ice bath, then filtered, the filter cake was washed with a small amount of ice water, and the dried crude product was purified by recrystalization with water to obtain 6-chloro-coumarin-3-carboxylic acid IIIc.

Step 2: Preparation of Theanine Ethyl Ester IIb

Theanine was dissolved in ethanol in an proportion of 87 g/L (namely, 87 g of theanine was dissolved in one liter of methanol), then sulfonyl chloride was slowly added into the system in an volume ratio of 55 ml, the mixture was stirred at room temperature for 1 h, then the resulting mixture was concentrated under reduced pressure to obtain theanine ethyl ester IIb.

Step 3: Preparation of TCIC Ic 20 g of theanine ethyl ester was dissolved in 2 L of anhydrous dichloromethane, 27 g of 6-chloro-coumarin-3-carboxylic acid was added, and 0.21 L of DIPEA (diisopropylethylamine) and 76 g of EDCI were added respectively. The mixture was stirred at room temperature for 1 h, then concentrated under reduced pressure to remove the solvent, the residue was purified by column chromatography, and the product of TCIC Ic was collected. The product was light yellow powdery solid and decomposed at or above the melting point of 242° C., and the structure characteristics of the compound were as follows:

$^1$H-NMR (500 MHz, CDCl$_3$) δ: 1.12 (t, J=7.25 Hz, 3H, CH$_3$), 1.28 (t, J=7.2 Hz, 3H, CH$_3$), 2.15-2.40 (m, 4H, CH$_2$), 3.26 (m, 2H, NH—CH$_2$), 4.14 (m, 1H, NH—CH), 4.21 (q, J=7.1 Hz, 2H, O—CH$_2$), 5.47 (br, 1H, NH), 6.91 (d, J=8.6

Hz, 1H, coumarin-8H), 7.25-7.28 (m, 2H, coumarin-5H, 7H), 8.33 (s, coumarin-4H), 12.93 (s, 1H, NH). $^{13}$C-NMR δ: 14.1 (CH$_3$), 14.8 (CH$_3$), 29.1 (CH$_2$), 32.0 (CH$_2$), 34.4 (CH$_2$), 61.6 (CH), 70.0 (CH$_2$), 118.7 (C), 119.3 (CH), 123.4 (C), 130.9 (CH), 132.7 (CH), 159.6 (C), 166.3 (C), 170.7 (C), 171.2 (C). ESI-MS (m/z): 407.1 [M-H]$^-$.

Embodiment 4

Preparation of the Compound Id and the Intermediate IIId Thereof

The general steps of the reaction are as follows:

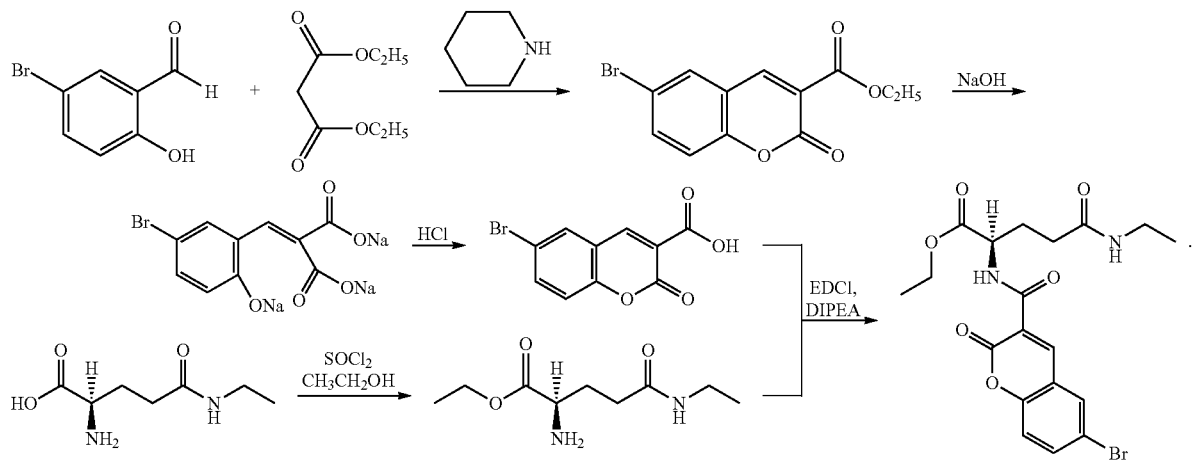

Step 1: Preparation of 6-bromo-coumarin-3-carboxylic acid IIId (1) 200 g of 5-bromosalicylaldehyde, 200 mL of diethyl malonate, 600 mL of anhydrous ethanol, 10 mL of piperidine (10.3 g) and 1 ml of glacial acetic acid were added in sequence; (2) the mixture was stirred and refluxed at 80° C. in water bath under anhydrous condition for 2 h, and cooled; (3) about 600 mL of cold water (0° C.) was added, the mixture was filtered after precipitation of crystals, and the filter cake was washed twice with 100 mL of 50% ethanol which was cooled by ice water (0° C.) to obtain 6-bromo-coumarin-3-carboxylate; (4) 124 g of ethyl 6-bromocoumarin-3-carboxylate and 100 g of sodium hydroxide were added respectively, then 500 mL of anhydrous ethanol and 500 mL of water were added, and the resulting mixture was heated and refluxed at 80° C. in water bath for about 2 h; and (5) the mixture was immediately placed into an 0° C. ice bath after the reaction, concentrated hydrochloric acid was added to enable the pH value of the system to be 2-3 so as to precipitate solids from the system, the mixture was cooled by the ice bath, then filtered, the filter cake was washed with a small amount of ice water, and the dried crude product was purified by recrystalization with water to obtain 6-bromo-coumarin-3-carboxylic acid IIId.

Step 2: Preparation of Theanine Ethyl Ester IIb

Theanine was dissolved in ethanol in an proportion of 87 g/L (namely, 87 g of theanine was dissolved in one liter of methanol), then sulfonyl chloride was slowly add into the system in a volume ratio of 55 ml, the mixture was stirred at room temperature for 1 h, and then the resulting mixture was concentrated under reduced pressure to obtain theanine ethyl ester IIb.

Step 3: Preparation of TBrC Id 20 g of theanine ethyl ester was dissolved in 2 L of anhydrous dichloromethane, 27 g of 6-bromo-coumarin-3-carboxylic acid was added, then 0.21 L of DIPEA (diisopropylethylamine) and 76 g of EDCI was added respectively. The mixture was stirred at room temperature for 1 h, then concentrated under reduced pressure to remove the solvent, the residue was purified by column chromatography, and the product was collected to obtain TBrC Id. The product was light yellow powdery solid and decomposed at or above the melting point of 211° C., and the structure characteristics of the compound were as follows:

$^1$H-NMR δ: 1.12 (t, J=7.2 Hz, 3H, CH$_3$), 1.28 (t, J=7.2 Hz, 3H, CH$_3$), 2.17-2.38 (m, 4H, CH$_2$), 3.26 (m, 2H, NH—CH$_2$), 4.15 (t, J=5.4 Hz, 1H, NH—CH), 4.21 (q, J=7.1 Hz, 2H, O—CH$_2$), 5.50 (br, 1H, NH), 6.87 (d, J=8.5 Hz, 1H, coumarin-8H), 7.39-7.42 (m, 2H, coumarin-5H, 7H), 8.32 (s, coumarin-4H), 12.95 (s, 1H, NH). $^{13}$C-NMR δ: 14.2 (CH$_3$), 14.8 (CH$_3$), 29.1 (CH$_2$), 32.0 (CH$_2$), 34.4 (CH$_2$), 61.6 (CH), 70.0 (CH$_2$), 110.3 (C), 119.2 (CH), 119.9 (C), 133.9 (CH), 139.7 (CH), 160.1 (C), 166.2 (C), 170.7 (C), 171.2 (C). ESI-MS (m/z): 451.0 [M-H]$^-$.

Embodiment 5

Preparation of the Compound Ie and the Intermediate IIIe Thereof

The general steps of the reaction are as follows:

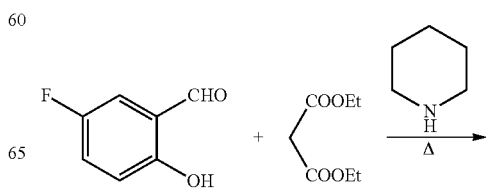

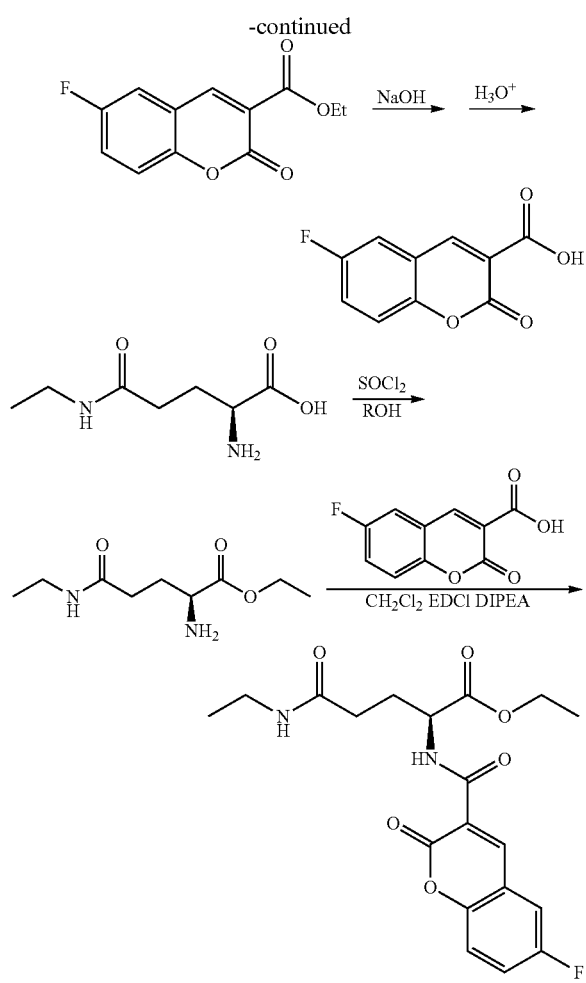

methanol), then sulfonyl chloride was slowly added into the system in a volume ratio of 55 ml, the mixture was stirred at room temperature for 1 h, and then the resulting mixture was concentrated under reduced pressure to obtain theanine ethyl ester IIb.

Step 3: Preparation of TFC Ie 20 g of theanine ethyl ester was dissolved in 2 L of anhydrous dichloromethane, 27 g of 6-fluoro-coumarin-3-carboxylic acid was added, then 0.21 L of DIPEA (diisopropylethylamine) and 76 g of EDCl was added respectively. The mixture was stirred at room temperature for 1 h, then concentrated under reduced pressure to remove the solvent, the residue was purified by column chromatography, and the product was collected to obtain TFC Ie. The product was light yellow powdery solid and decomposed at or above the melting point of 300° C., and the structure characteristics of the compound were as follows:

m.p.: 109-111° C. $^1$H-NMR δ: 1.12 (t, J=7.2 Hz, 3H, $CH_3$), 1.28 (t, J=7.2 Hz, 3H, $CH_3$), 2.17-2.38 (m, 4H, $CH_2$), 3.26 (m, 2H, NH—$CH_2$), 4.15 (t, J=5.4 Hz, 1H, NH—CH), 4.21 (q, J=7.1 Hz, 2H, O—$CH_2$), 5.50 (br, 1H, NH), 6.87 (d, J=8.5 Hz, 1H, coumarin-8H), 7.39-7.42 (m, 2H, coumarin-5H, 7H), 8.32 (s, coumarin-4H), 12.95 (s, 1H, NH). $^{13}$C-NMR δ: 14.2 ($CH_3$), 14.8 ($CH_3$), 29.1 ($CH_2$), 32.0 ($CH_2$), 34.4 ($CH_2$), 61.6 (CH), 70.0 ($CH_2$), 110.3 (C), 119.2 (CH), 119.9 (C), 133.9 (CH), 139.7 (CH), 160.1 (C), 166.2 (C), 170.7 (C), 171.2 (C). ESI-MS (m/z): 451.0 [M-H]$^-$.

Embodiment 6

Preparation of the Compound If and the Intermediate IIIf Thereof

The general steps of the reaction are as follows:

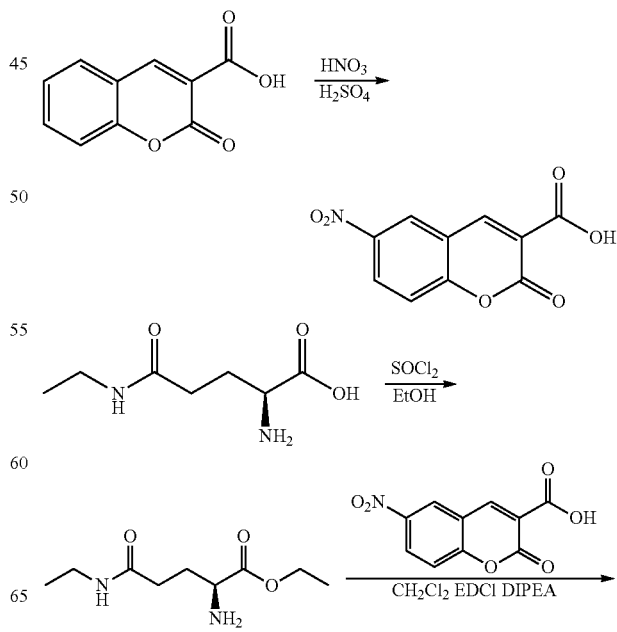

Step 1: Preparation of 6-fluoro-coumarin-3-carboxylic acid IIIe (1) 200 g of 5-fluorosalicylaldehyde, 200 mL of diethyl malonate, 600 mL of anhydrous ethanol, 10 mL of piperidine (10.3 g) and 1 ml of glacial acetic acid were added in sequence; (2) the mixture was stirred and refluxed at 80° C. in water bath for 2 h under anhydrous condition, and cooled; (3) about 600 mL of cold water (0° C.) was added, the mixture was filtered after precipitation of crystals, and washed twice with 100 mL of 50% ethanol which was cooled by the ice water (0° C.) to obtain 6-fluorocoumarin-3-carboxylate; (4) 124 g of ethyl 6-fluorocoumarin-3-carboxylate and 100 g of sodium hydroxide were added respectively, then 500 mL of anhydrous ethanol and 500 mL of water were added, the mixture was heated and refluxed at 80° C. in water bath for about 2 h; and (5) the mixture was immediately placed into an 0° C. ice bath after the reaction, concentrated hydrochloric acid was added to enable the pH value of the system to be 2-3 so as to precipitate solids from the system, the system was cooled by the ice bath, then filtered, washed with a small amount of ice water, and the dried crude product was purified by recrystalization with the water to obtain 6-fluorocoumarin-3-carboxylic acid IIIe.

Step 2: Preparation of Theanine Ethyl Ester IIb

Theanine was dissolved in ethanol in an proportion of 87 g/L (namely, 87 g of theanine was dissolved in one liter of

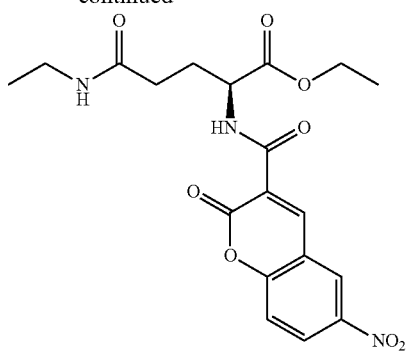

Specific Step 1: Preparation of 6-nitro-coumarin-3-carboxylic acid IIIf 50 g of coumarin-3-acid was dissolved in 240 mL of concentrated sulfuric acid, cooled to −10° C., a mixed acid solution of concentrated nitric acid and concentrated sulfuric acid (80 mL, wherein the volume ratio of concentrated nitric acid to concentrated sulfuric acid is 1:3) was added, the mixture was stirred at 0° C. for 1 h, then the temperature was raised to room temperature and the mixture was reacted for further 1 h. The reaction solution was poured into 5000 mL of ice water, stood for crystallization, the crystal was filtered, washed with the ice water, and dried to obtain 6-nitrocoumarin-3-carboxylic acid IIIf which was light yellow amorphous solid.

Step 2: Preparation of Theanine Ethyl Ester IIb

Theanine was dissolved in ethanol in an proportion of 87 g/L (namely, 87 g of theanine was dissolved in one liter of methanol), then sulfonyl chloride was slowly added into the system in a volume ratio of 55 ml, the mixture was stirred at room temperature for 1 h, and then the resulting mixture was concentrated under reduced pressure to obtain theanine ethyl ester IIb.

Step 3: Preparation of TNC If 20 g of theanine ethyl ester was dissolved in 2 L of anhydrous dichloromethane, 27 g of 6-nitro-coumarin-3-carboxylic acid was added, then 0.21 L of DIPEA (diisopropylethylamine) and 76 g of EDCI were added respectively. The mixture was stirred at room temperature for 1 h, concentrated under reduced pressure to remove the solvent, the residue was purified by column chromatography, and the product was collected to obtain TNC If. The product was light yellow powdery solid and decomposed at or above the melting point of 165° C., and the structure characteristics of the compound were as follows:

m.p.: 109-111° C. $^1$H-NMR δ: 1.12 (t, J=7.2 Hz, 3H, CH$_3$), 1.28 (t, J=7.2 Hz, 3H, CH$_3$), 2.17-2.38 (m, 4H, CH$_2$), 3.26 (m, 2H, NH—CH$_2$), 4.15 (t, J=5.4 Hz, 1H, NH—CH), 4.21 (q, J=7.1 Hz, 2H, O—CH$_2$), 5.50 (br, 1H, NH), 6.87 (d, J=8.5 Hz, 1H, coumarin-8H), 7.39-7.42 (m, 2H, coumarin-5H, 7H), 8.32 (s, coumarin-4H), 12.95 (s, 1H, NH). $^{13}$C-NMR δ: 14.2 (CH$_3$), 14.8 (CH$_3$), 29.1 (CH$_2$), 32.0 (CH$_2$), 34.4 (CH$_2$), 61.6 (CH), 70.0 (CH$_2$), 110.3 (C), 119.2 (CH), 119.9 (C), 133.9 (CH), 139.7 (CH), 160.1 (C), 166.2 (C), 170.7 (C), 171.2 (C). ESI-MS (m/z): 451.0 [M-H]$^-$.

Embodiment 7

Preparation of the Compounds Ig and Ih and the Intermediates IIIg and IIIh Thereof The general steps of the reaction are as follows:

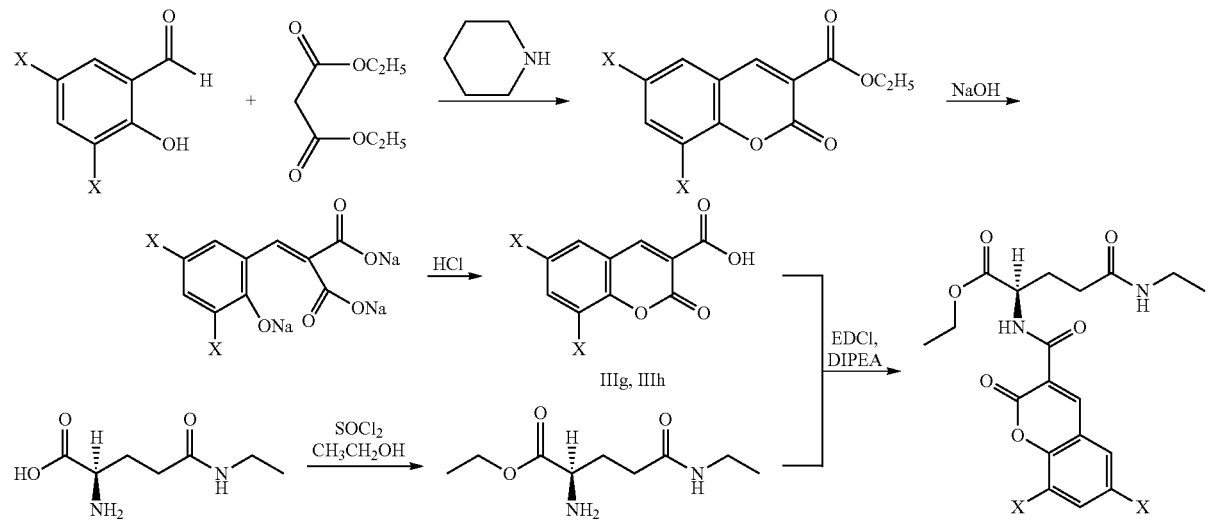

When X=Cl and IIIg=DClC, the final product is Ig; and when X=Br and IIIh=DBrC, the final product is Ih.

Step 1: Preparation of 6,8-dichloro-coumarin-3-carboxylic acid IIIg and 6,8-dibromo-coumarin-3-carboxylic acid IIIh (1) 200 g of 3,5-dichlorosalicylaldehyde or 3,5-dibromo-salicylaldehyde, 200 mL of diethyl malonate, 600 mL of anhydrous ethanol, 10 mL of piperidine (10.3 g), and 1 ml of glacial acetic acid were added in sequence; (2) the mixture was stirred and refluxed at 80° C. in water bath for 2 h under anhydrous condition, and cooled; (3) about 600 mL of cold water (0° C.) was added, the mixture was filtered after precipitation of crystals, and the crystal was washed twice with 100 mL of 50% ethanol which was cooled by the ice water (0° C.) to obtain 6,8-dichlorocoumarin-3-carboxylate or 6,8-dibromocoumarin-3-carboxylate; (4) 124 g of 6,8-dichlorocoumarin-3-carboxylate or 6,8-dibromocoumarin-3-carboxylate, and 100 g of sodium hydroxide were added respectively, then 500 mL of anhydrous ethanol and 500 mL of water were added, the mixture was heated and refluxed at 80° C. in water bath for about 2 h; and (5) the resulting mixture was immediately placed into an 0° C. ice bath after the reaction, concentrated hydrochloric acid was added to enable the pH value of the system to be 2-3 so as to precipitate solids from the system, the system was cooled by the ice bath, then filtered, washed with a small amount of ice water, and the dried crude product was purified by recrystalization with water to obtain 6,8-dichlorocoumarin-3-carboxylic acid or 6,8-dibromocoumarin-3-carboxylic acid.

Step 2: Preparation of Theanine Ethyl Ester IIb

Theanine was dissolved in ethanol in an proportion of 87 g/L (namely, 87 g of theanine was dissolved in one liter of methanol), then sulfonyl chloride was slowly added into the system in a volume ratio of 55 ml, the mixture was stirred at room temperature for 1 h, and then the resulting mixture was concentrated under reduced pressure to obtain theanine ethyl ester.

Step 3: Preparation of DTCIC Ig and DTBrC Ih 20 g of theanine ethyl ester was dissolved in 2 L of anhydrous dichloromethane, 27 g of 6,8-dichloro-coumarin-3-carboxylic acid or 6,8-dibromocoumarin-3-carboxylic acid was added, then 0.21 L of DIPEA (diisopropylethylamine) and 76 g of EDCI were added respectively. The mixture was stirred at room temperature for 1 h, then the mixture was concentrated under reduced pressure to remove the solvent, the residue was purified by column chromatography, and the product was collected to obtain DTCIC Ig or DTBrC Ih. The product was light yellow powdery solid and decomposed at or above the melting point of 136° C. or 121° C., and the structure characteristics of the two compounds were as follows respectively:

(I) DTCIC: $^1$H-NMR δ: 1.11 (t, J=7.2 Hz, 3H, NHCH$_2$C$\underline{H}_3$), 1.28 (t, J=7.1 Hz, 3H, OCH$_2$C$\underline{H}_3$), 2.19-2.40 (m, 4H, C$\underline{H}_2$C$\underline{H}_2$), 3.20-3.29 (m, 2H, NH$\underline{CH}_2$CH$_3$), 4.18-4.25 (m, 3H), 6.20 (br s, 1H, NH), 7.19 (d, J=2.4 Hz, 1H, coumarin-5H), 7.39 (d, J=2.4 Hz, 1H, coumarin-7H), 8.35 (s, coumarin-4H), 14.02 (br s, 1H, NH); 12.95 (s, 1H, NH). $^{13}$C-NMR δ: 13.92 (CH$_3$), 14.52 (CH$_3$), 28.90 (CH$_2$), 31.45 (CH$_2$), 34.16 (CH$_2$), 61.49 (CH), 69.08 (CH$_2$), 119.15 (C), 122.43 (CH), 122.65 (C), 129.31 (CH), 132.31 (CH), 156.07 (C), 165.68 (C), 170.14 (C), 171.04 (C). ESI-MS (m/z): 441.0 [M-H]$^-$.

(II) DTBrC: 1H-NMR δ: 1.12 (t, J=7.3 Hz, 3H, NHCH2CH3), 1.28 (t, J=7.2 Hz, 3H, OCH2CH3), 2.17-2.28 (m, 4H, CH2CH2), 3.22-3.29 (m, 2H, NHCH2CH3), 4.18-4.26 (m, 3H), 5.75 (br s, 1H, NH), 7.38 (d, J=2.3 Hz, 1H, coumarin-5H), 7.71 (d, J=2.3 Hz, 1H, coumarin-7H), 8.32 (s, coumarin-4H), 14.12 (br s, 1H, NH); 12.95 (s, 1H, NH). 13C-NMR (100 MHz, CDCl3) δ: 14.07 (CH3), 14.71 (CH3), 28.99 (CH2), 31.65 (CH2), 34.34 (CH2), 61.66 (CH), 69.16 (CH2), 109.80 (C), 112.09 (CH), 119.82 (C), 133.14 (CH), 137.96 (CH), 157.48 (C), 165.63 (C), 170.20 (C), 171.04 (C). ESI-MS (m/z): 528.5 [M-H]−.

Embodiment 8

Inactivation Effects of Compounds and Intermediates Thereof as Obtained in Embodiments 1-7, as Well as the Compound as Represented by Formula (IIIa) Against Various Human Cancer Cells The inactivation effects of the compounds and the intermediates thereof as obtained in embodiments 1-7, a positive control anti-cancer drug and the like against various human cancer cells cultured in-vitro were determined according to the literature method (Zhang Y, et al., Cytotechnology 2009, 59 (3): 191-200), and the results were shown in Table 1.

Cell lines and cell culture: human lung cancer cells A549 and H460, human breast cancer cells MCF-7 and MDA-MB-231, human gastric cancer cells BGC-823, human prostate cancer cells PC-3, human chronic leukemia cells K562, human lymphoma cells U937, human liver cancer cells SMMC7721 and HepG2, human colon cancer cells HT29, human pancreatic cancer cells PANC-1 and BxPC3, human cervical cancer Hela cell lines, human brain tumor cells Daoy, human neuroma cells D54 and human oral epidermoid cancer cells KBV200 line with strong drug resistance, mouse melanoma cells B16, and highly metastatic Lewis lung cancer cell lines were purchased from American Type Culture Collection of the U.S. These cells were cultured with DMEM and RPMI-1640 culture solutions separately.

2. Instruments and Equipment:

A carbon dioxide incubator: 3111, Thermo Company of the U.S.; and an inverted fluorescent microscope: TE2000-U, Nikon Company of Japan. An inverted microscope: CKX31, Olympus Company of Japan; a table high-speed refrigerated centrifuge: 5810R, Eppendorf Company of Germany; a micropipette: Eppendorf Company of Germany; a cell culture plastic plate (96-well): BD company; a microplate reader: a SYNERGY HT multifunctional microplate reader, BIO-TEK Company of the U.S.; an ice making machine: XB 70, GRANT Company; and an in-vivo X-ray and fluorescence imaging instrument for living body: Kodak Image Station 2000: Carestream Health Company of the U.S.

A MTT method was adopted for testing the inhibitory effects against the growth of the cancer cells in-vitro of the compounds and the intermediates thereof as obtained in embodiments 1-7, as well as the compound as represented by formula (IIIa), and a trypan blue staining method was used for verification. The procedure was as follows:

3. Main Reagents, Cell Lines and Instruments:

The cancer cell lines and the instruments were described as above 1 and 2.

RPMI1640 and DMEM culture solutions: Hyclone Company;

Inactivated fetal bovine serum: Hyclone Company;

Trypsin: Amersco Company; 0.4% trypan blue: Sigma Company;

Methyl thiazolyl tetrazolium (MTT): Sigma Company;

2. Experimental Procedure:

(1) 0.25% trypsin was used to digest cancer cells in a logarithmic growth phase to prepare a single-cell suspension, the concentration of cells was adjusted to 5×10$^4$/mL, and the adjusted suspension was inoculated into a 96-well culture plate with 100 μl per well;

(2) The culture plate was transferred into a 37° C. incubator with a saturated humidity and 5% of CO2 and cultured for 24 h; the compounds and the intermediates thereof obtained in embodiments 1-7 and the compound as represented by formula (IIIa) or the positive control anti-cancer drug with the concentration of 1-1000 μM/L were added to enable the final concentration to be 0.1-1500 μM/L. Control wells (only added with 200 μl of cell suspension) and drug-free blank control wells (containing the solvent of 0.01% DMSO) were set, each group included 8 wells, and the plate was placed into the 37° C. incubator with saturated humidity and 5% of CO2 for culturing;

(3) The 96-well plate was taken out at 48 h and 72 h after dosing, the original culture medium was carefully removed by suction, 100 μl of serum-free DMEM culture medium and 10 μl of MTT (5 mg/mL) solution were added in each well. The plate was continuously cultured for another 4 h and then the culture was terminated;

(4) The supernatant in the wells was carefully removed by suction, each well was added with 150 μl of DMSO and shaked at room temperature for 10-15 min to fully dissolve crystals.

(5) Colorimetric analysis: the wavelength was selected as 570 nm, the light absorbance (A value) of each well was determined on the microplate reader and the results were recorded; the experiment was repeated for three times;

(6) the experimental results were calculated according to the following formula: relative survival rate=(A value of each experimental group/A value of cell control group)× 100%

Calculation of median-effect concentration (IC50, namely the drug concentration at which the inhibition rate is 50%, also known as half inhibitory concentration):

IC50 of the detected component was calculated by using a regression equation.

3. Experimental Results (See Table 1)

TABLE 1

Inhibitory effects of compounds and intermediates thereof as obtained in embodiments 1-7 against the growth of human cancer cells

| Cell strain | Drug concentration (mM/L) | | | | | |
|---|---|---|---|---|---|---|
| | Compound Ia | Compound IIa | Compound Ib | Compound Ic | Compound IIIa | Compound IIIc |
| A549 | 0.3 ± 0.06 * | 0.65 ± 0.03 * | 0.125 ± 0.05 * | 0.128 ± 0.06 * | >0.7 * | 0.6 ± 0.03 * |
| H460 | 0.23 * ± 0.06 | 0.5 ± 0.04 | 0.113 ± 0.04 | 0.106 ± 0.05 * | >0.70 * | 0.35 ± 0.05 * |
| MCF-7 | 0.22 * ± 0.05 | 0.45 ± 0.06 | 0.103 ± 0.05 | 0.095 * ± 0.04 | >0.70 * | 0.3 * ± 0.04 |
| MDA-MB-231 | 0.24 * ± 0.06 | 0.48 ± 0.06 | 0.109 ± 0.05 | 0.87 * ± 0.04 | >0.7 * | 0.5 L * ± 0.06 |
| BGC-823 | 0.123 * ± 0.05 | 0.31 ± 0.06 | 0.127 ± 0.05 | 0.066 * ± 0.05 | >0.70 * | 0.30 * ± 0.05 |
| PC-3 | 0.146 * ± 0.03 | 0.35 * ± 0.05 | 0.125 * ± 0.04 | 0.105 * ± 0.04 | >0.50 | 0.5 * ± 0.05 |
| U937 | 0.056 ± 0.01 * | 0.35 * ± 0.03 | 0.09 * ± 0.3 | 0.052 * ± 0.03 | >0.70 * | 0.5 * ± 0.1 |
| PANC-1 | 0.067 ± 0.03 * | 0.28 * ± 0.04 | 0.065 * ± 0.03 | 0.054 * ± 0.03 | >0.70 * | 0.5 * ± 0.01 |
| Hela | 0.064 ± 0.02 * | 0.33 * ± 0.04 | 0.053 * ± 0.02 | 0.35 * ± 0.1 | >0.70 * | 0.6 * ± 0.01 |
| S-7721 | 0.075 * ± 0.03 * | 0.23 * ± 0.04 | 0.017 * ± 0.3 | 0.075 * ± 0.03 | >0.50 * | 0.5 * ± 0.1 |
| HT29 | 0.062 * ± 0.2 | 0.25 * ± 0.04 | 0.105 * ± 0.05 | 0.105 * ± 0.05 | >0.70 * | 0.7 * ± 0.05 |
| B16 | 0.145 * ± 0.05 | 0.45 * ± 0.02 | 0.11 * ± 0.02 | 0.125 * ± 0.05 | >0.70 * | 0.6 * ± 0.02 |
| K562 | 0.248 * ± 0.05 | 0.35 * ± 0.02 | 0.15 * ± 0.02 | 0.105 * ± 0.15 | >0.70 * | 0.6 * ± 0.02 |
| LLC | 0.185 * ± 0.04 | 0.1 * ± 0.03 | 0.115 * ± 0.02 | 0.131 * ± 0.04 | >0.70 * | 0.4 * ± 0.03 |
| BxPc3 | 0.35 * ± 0.01 | 0.6 * ± 0.02 | 0.105 * ± 0.02 | 0.089 * ± 0.03 | >0.70 * | 0.5 * ± 0.03 |
| HepG2 | 0.25 * ± 0.05 | 0.6 * ± 0.02 | 0.225 * ± 0.03 | 0.093 * ± 0.03 | >0.70 * | 0.3 * ± 0.03 |
| Caski | 0.21 * ± 0.04 | 0.32 * ± 0.03 | 0.116 * ± 0.05 | 0.086 * ± 0.02 | >0.70 * | 0.4 * ± 0.03 |
| Daoy | 0.25 * ± 0.03 | 0.4 * ± 0.02 | 0.135 * ± 0.02 | 0.086 * ± 0.03 | >0.70 * | 0.4 * ± 0.03 |
| D54 | 0.16 * ± 0.03 | 0.4 * ± 0.03 | 0.165 * ± 0.03 | 0.098 * ± 0.02 | >0.70 * | 0.3 * ± 0.03 |
| KBV200 | 0.24 * ± 0.02 | 0.38 * ± 0.04 | 0.136 * ± 0.02 | 0.097 * ± 0.02 | >0.70 * | 0.4 * ± 0.03 |

| Cell strain | Drug concentration (mM/L) | | | Positive anti-cancer drug control | Solvent control |
|---|---|---|---|---|---|
| | Compound IIb | Compound Id | Compound IIId * | | |
| A549 | 0.5 ± 0.03 * | 0.139 ± 0.05 * | 0.6 mM/L * ± 0.03 | Vincristine 0.22 * ± 0.04 | – |
| H460 | 0.4 ± 0.01 * | 0.101 ± 0.05 | 0.5 * ± 0.03 | Daunorubicin 0.063 * ± 0.04 | – |
| MCF-7 | 0.3 * ± 0.02 | 0.102 * ± 0.05 | 0.4 * ± 0.02 | Daunorubicin 0.058 * ± 0.04 | – |
| MDA-MB-231 | 0.4 * ± 0.06 | 0.091 * ± 0.06 | 0.5 * ± 0.03 | Vincristine 0.13 * ± 0.04 | – |
| BGC-823 | 0.6 * ± 0.05 | 0.065 * ± 0.06 | 0.70 ± 0.05 | Genistein 0.135 * ± 0.05 Daunorubicin 0.068 * ± 0.03 | – |
| PC-3 | 0.4 * ± 0.05 | 0.11 * ± 0.04 | 0.5 * ± 0.05 | Daunorubicin 0.051 * ± 0.03 | – |
| U937 | 0.4 * ± 0.1 | 0.124 * ± 0.3 | 0.5 * ± 0.05 | Carboplatin 0.058 ± 0.03 * | – |
| PANC-1 | 0.4 * ± 0.01 | 0.055 * ± 0.03 | 0.5 * ± 0.03 | Daunorubicin 0.055 * ± 0.03 | – |
| Hela | 0.5 * ± 0.01 | 0.075 * ± 0.01 | 0.6 * ± 0.03 | Cisplatin 0.066 * ± 0.006 | – |
| S-7721 | 0.4 * ± 0.1 | 0.065 * ± 0.3 | 0.5 * ± 0.1 | Vincristine 0.078 ± 0.03 * | – |
| HT29 | 0.6 * ± 0.05 | 0.045 * ± 0.05 | 0.7 * ± 0.05 | Daunorubicin 0.063 * ± 0.03 | – |

TABLE 1-continued

Inhibitory effects of compounds and intermediates thereof as obtained
in embodiments 1-7 against the growth of human cancer cells

| | | | | | |
|---|---|---|---|---|---|
| B16 | 0.5 * ± 0.02 | 0.12 * ± 0.02 | 0.6 * ± 0.02 | Cisplatin 0.067 ± 0.03 * | – |
| K562 | 0.6 * ± 0.02 | 0.125 * ± 0.05 | 0.6 * ± 0.05 | Etoposide 0.085 * ± 0.03 | – |
| LLC | 0.3 * ± 0.02 | 0.116 * ± 0.04 | 0.4 * ± 0.03 | Norcantharidin 0.015 * ± 0.01 | – |
| BxPc3 | 0.3 * ± 0.02 | 0.116 * ± 0.04 | | Noncantharidin 0.06 * ± 0.03 | – |
| HepG2 | 0.3 * ± 0.02 | 0.125 * ± 0.04 | | Vincristine 0.037 * ± 0.01 | – |
| Caski | 0.3 * ± 0.03 | 0.101 * ± 0.04 | | Etoposide 0.089 * ± 0.03 | – |
| Daoy | 0.4 * ± 0.02 | 0.128 * ± 0.03 | | Cisplatin 0.0016 * ± 0.0001 | – |
| D54 | 0.3 * ± 0.02 | 0.092 * ± 0.04 | | Cisplatin 0.021 * ± 0.001 | – |
| KBV200 | 0.3 * ± 0.03 | 0.112 * ± 0.02 | | Daunorubicin 0.001 * ± 0.0003 | – |

| | Drug concentration (mM/L) | | | | |
|---|---|---|---|---|---|
| Cell strain | Compound Ie * | Compound IIIe * | Compound If * | Compound IIIf * | Compound Ig * |
| A549 | 0.141 * ± 0.04 | 0.45 * ± 0.03 | 0.122 * ± 0.04 | 0.58 * ± 0.04 | 0.045 * ± 0.003 |
| H460 | 0.10 * ± 0.03 | 0.45 * ± 0.05 | 0.10 * ± 0.04 | 0.46 * ± 0.04 | 0.093 * ± 0.06 |
| MCF-7 | 0.115 * ± 0.03 | 0.39 * ± 0.02 | 0.112 * ± 0.04 | 0.4 * ± 0.04 | 0.075 * ± 0.03 |
| MDA-MB231 | 0.09 * ± 0.03 | 0.52 * ± 0.03 | 0.110 * ± 0.04 | 0.47 * ± 0.04 | 0.092 * ± 0.04 |
| BGC-823 | 0.143 * ± 0.03 | 0.70 * ± 0.05 | 0.115 * ± 0.06 | 0.65 * ± 0.02 | 0.06 * ± 0.005 |
| PC-3 | 0.127 * ± 0.06 | 0.52 * ± 0.05 | 0.171 * ± 0.05 | 0.53 * ± 0.04 | 0.045 * ± 0.004 |
| U937 | 0.126 * ± 0.6 | 0.56 * ± 0.06 | 0.121 * ± 0.4 | 0.45 * ± 0.06 | 0.038 * ± 0.02 |
| PANC-1 | 0.072 * ± 0.01 | 0.48 * ± 0.03 | 0.077 * ± 0.03 | 0.43 * ± 0.04 | 0.071 * ± 0.006 |
| Hela | 0.071 * ± 0.03 | 0.6 * ± 0.03 | 0.071 * ± 0.03 | 0.58 * ± 0.05 | 0.066 * ± 0.004 |
| S-7721 | 0.061 * ± 0.3 | 0.49 * ± 0.6 | 0.061 * ± 0.3 | 0.46 * ± 0.6 | 0.078 * ± 0.04 |
| HT29 | 0.24 * ± 0.05 | 0.57 * ± 0.05 | 0.153 * ± 0.04 | 0.46 * ± 0.04 | 0.099 * ± 0.05 |
| B16 | 0.23 * ± 0.05 | 0.6 * ± 0.06 | 0.28 * ± 0.06 | 0.67 * ± 0.03 | 0.125 * ± 0.05 |
| K562 | 0.13 * ± 0.05 | 0.3 * ± 0.05 | 0.091 * ± 0.04 | 0.3 * ± 0.04 | 0.057 * ± 0.03 |
| LLC | 0.11 * ± 0.03 | 0.38 * ± 0.03 | 0.10 * ± 0.04 | 0.37 * ± 0.06 | 0.036 * ± 0.02 |
| BxPc3 | 0.26 * ± 0.05 | 0.5 * 0.06 | 0.18 * ± 0.03 | 0.114 * ± 0.04 | 0.119 * ± 0.04 |
| HepG2 | 0.23 * ± 0.09 | 0.4 * ± 0.08 | 0.13 * ± 0.06 | 0.36 * ± 0.07 | 0.046 * ± 0.02 |
| Caski | 0.23 * ± 0.04 | 0.38 * ± 0.06 | 0.12 * ± 0.04 | 0.3 * ± 0.05 | 0.036 * ± 0.02 |
| Daoy | 0.21 * ± 0.06 | 0.5 * ± 0.06 | 0.129 * ± 0.04 | 0.4 * ± 0.06 | 0.11 * ± 0.04 |
| D54 | 0.15 * ± 0.05 | 0.3 * ± 0.03 | 0.105 * ± 0.03 | 0.3 * ± 0.02 | 0.079 * ± 0.02 |
| KBV200 | 0.21 * ± 0.04 | 0.3 * ± 0.06 | 0.102 * ± 0.02 | 0.3 * ± 0.06 | 0.084 * ± 0.03 |

| | Drug concentration (mM/L) | | | | |
|---|---|---|---|---|---|
| Cell strain | Compound Ih * | Compound IIIg * | Compound IIIh * | Positive anti-cancer drug control | Solvent control |
| A549 | 0.056 * ± 0.004 | 0.33 * ± 0.03 | 0.45 * ± 0.02 | Vincristine 0.22 * ± 0.04 * | – |
| H460 | 0.109 * ± 0.05 | 0.4 * ± 0.06 | 0.55 * ± 0.06 | Daunorubicin 0.063 * ± 0.04 | – |
| MCF-7 | 0.091 * ± 0.04 | 0.41 * ± 0.02 | 0.45 * ± 0.02 | Daunorubicin 0.058 * ± 0.04 | – |
| MDA-MB231 | 0.098 * ± 0.04 | 0.46 * ± 0.03 | 0.42 * ± 0.03 | Vincristine 0.13 * ± 0.04 | – |
| BGC-823 | 0.085 * ± 0.03 | 0.38 * ± 0.03 | 0.48 * ± 0.04 | Genistein 0.135 * ± 0.03 Daunorubicin ±0.05 | – |
| PC-3 | 0.087 * ± 0.03 | 0.31 * ± 0.05 | 0.41 * ± 0.05 | Daunorubicin 0.051 * ± 0.03 | – |
| U937 | 0.057 * ± 0.03 | 0.35 * ± 0.03 | 0.39 * ± 0.04 | Carboplatin 0.058 ± 0.03 * | – |
| PANC-1 | 0.078 * ± 0.03 | 0.43 * ± 0.01 | 0.48 * ± 0.01 | Daunorubicin 0.055 * ± 0.03 | – |
| Hela | 0.058 * ± 0.03 | 0.26 * ± 0.01 | 0.29 * ± 0.02 | Cisplatin 0.066 * ± 0.06 | – |
| S-7721 | 0.086 * ± 0.04 | 0.49 * ± 0.1 | 0.53 * ± 0.1 | Vincristine 0.078 * ± 0.03 * | – |
| HT29 | 0.108 * ± 0.05 | 0.48 * ± 0.04 | 0.59 * ± 0.05 | Daunorubicin 0.063 * ± 0.03 * | – |
| B16 | 0.146 * ± 0.05 | 0.5 * ± 0.06 | 0.46 * ± 0.02 | Cisplatin 0.067 * ± 0.03 * | – |
| K562 | 0.079 * ± 0.03 | 0.42 * ± 0.06 | 0.48 * 0.06 | Etoposide 0.085 * ± 0.03 | |

TABLE 1-continued

Inhibitory effects of compounds and intermediates thereof as obtained
in embodiments 1-7 against the growth of human cancer cells

| | | | | | |
|---|---|---|---|---|---|
| LLC | 0.053 * ± 0.04 | 0.25 * ± 0.05 | 0.35 * 0.06 | Noncantharidin 0.015 * ± 0.001 | – |
| BxPc3 | 0.128 * ± 0.04 | 0.3 * ± 0.06 | 0.4 * ± 0.05 | Noncantharidin 0.06 * ± 0.02 | |
| HepG2 | 0.056 * ± 0.03 | 0.42 * ± 0.02 | 0.145 * 0.06 | Vincristine 0.037 * ± 0.02 | |
| Caski | 0.053 * ± 0.03 | 0.25 * ± 0.06 | 0.135 * ± 0.03 | Etoposide 0.089 * ± 0.03 | |
| Daoy | 0.121 * ± 0.04 | 0.35 * ± 0.06 | 0.35 * ± 0.03 | Cisplatin 0.0016 * ± 0.001 | – |
| D54 | 0.087 * ± 0.03 | 0.3 * ± 0.05 | 0.3 * ± 0.06 | Cisplatin 0.021 * ± 0.001 | – |
| KBV200 | 0.072 * ± 0.03 | 0.3 * ± 0.06 | 0.3 * ± 0.03 | Daunorubicin 0.001 * ± 0.0001 | – |

Note:
* $p < 0.05$, compared with the solvent control group; and as for the method for testing the growth of the cells by MTT, please see the above experimental method. The above results were verified by a trypan blue staining method, and the results of the trypan blue staining method showed the same effect of the compounds.
§ refers to the drug concentration (IC50) at which 50% cancer cells survived 72 h after treatment with the listed compound respectively.
A549: human lung cancer cells; NCI-H460: H460 human lung cancer cells; MB231: MDA-MB231 (- highly metastatic human breast cancer cells with negative estrogen receptor); MCF-7: estrogen receptor-positive human breast cancer cells; S-7721: SMMC7721 (human liver cancer cells); PANC-1: human pancreatic cancer cells; Hela: human cervical cancer cells; LLC: Lewis lung cancer (highly metastatic mouse lung cancer) cells; BGC-823: human gastric cancer cells; PC-3: human prostate cancer cells; U937: human histiocytic lymphoma cells; human liver cancer cells; HT29: human colon cancer cells; B16: melanoma cells; K562: human leukemia cells; BxPc3: human pancreatic cancer cells; HepG2: human liver cancer cells; Caski: human cervical cancer cells; Daoy: human brain tumor cells; D54: neuroma cells; and KBV200: human oral epidermoid cancer cells with strong drug resistance.

Embodiment 9

Experiments of Compounds and Intermediates Thereof as Obtained in Embodiments 1-7 in Inhibition of the Growth of a Variety of Human Cancer Xenografts in Nude Mice, and of Metastasis of Mouse Lung Cancer The inhibitory effects of the compounds and the intermediates thereof as obtained in embodiments 1-7 against in-vivo growth of a variety of human cancer xenografts in animal were determined according to the literature method (George N. Naumov, et al. Combined Vascular Endothelial Growth Factor Receptor and Epidermal Growth Factor Receptor (EGFR) Blockade Inhibits Tumor Growth in Xenograft Models of EGFR Inhibitor Resistance Clin Cancer Res 2009, 15:3484-3494; Yang Zhenzhou, et al.), and the results were shown in Table 2.

1. Experimental Animals, Cell Lines, Main Reagents and Instruments:

SPF-level BALB/c nude mice and C57/BL6J black mice, 4-5 weeks old, 18-22 g, female, purchased from Beijing Huafukang Experimental Animal Center, with animal license number of SCXK (Beijing) 2009-0004, and raised in an SPF-grade animal laboratory; an IVC (independent ventilated cage): Suzhou Suhang Technology Equipment Co., Ltd.; and human lung cancer cells A549, estrogen receptor-negative human breast cancer cells MDA-MB231, estrogen receptor-positive human breast cancer cells MCF-7, human liver cancer cells SMMC7721, human pancreatic cancer cells PANC-1, human cervical cancer cells Hela, highly metastatic Lewis lung cancer cell lines, and other instruments were as described above. RPMI1640 and DMEM culture solutions: Hyclone Company; inactivated fetal bovine serum: Hyclone Company, preserved at −20° C.; trypsin: Amersco Company; and 0.4% trypan blue: Sigma Company;

2. Experimental Procedure:

(1) Cell culture and establishment of animal models with transplanted tumor: human cancer cell strains were separately cultured in a DMEM culture solution or an RPMI-1640 culture solution containing 10% fetal bovine serum under the conditions of 37° C. and 5% of CO2. Cells in a logarithmic growth phase were collected to prepare a single-cell suspension with the concentration of 2×107/ml, 0.1 ml of suspension was separately subcutaneously inoculated into the back part of the thigh of each nude mouse in an ultra-clean workbench, and each injection point was observed every day to check whether there was redness, swelling, ulceration or not. After 2-5 weeks, obvious skin rashes appeared at the injection parts, the subcutaneous nodules with a diameter of about 10-15 mm appeared in all the nude mice and the transplanted tumor models were established; and for the establishment of mouse Lewis lung cancer metastasis models, a single-cell suspension with the concentration of 6×106/ml was prepared, 0.1 ml of the cell suspension was intravenously injected into tail veins of the C57/BL6J black mice, drug was administered from the second day after grouping, and the drug doses and ways in the nude mice were described as below.

(2) Grouping of mice and drug delivery: the subcutaneous xenograft model nude mice were randomly divided into three groups with 7 mice in each group after 2-5 weeks of inoculation; a negative control group (with solvent of 0.05% DMDO), intraperitoneal injection of 0.2 ml/mouse and once a day; the drugs and the components were intraperitoneally injected (60-90 mg/kg): positive control groups, anti-cancer drug cisplatin (1.5 mg/kg/day), cyclophosphamide (60 mg/kg/2 day) and endostar (8 mg/kg), and the groups of the compounds and the intermediates thereof as obtained in embodiments 1-7, once a day, and the medication was performed for 3-5 weeks.

For the detection of the effect of the drugs on enzyme activity of EZH2 and HDAC of in-vivo tumors, the tumors were separately excised after 6 h of medication, total proteins and nucleoproteins were extracted separately to detect and analyze the activity of the enzyme. The tumors were taken out after the mice were treated with the negative control of DMSO (0.05%) solvent, the positive control of SAHA (suberoylanilide hydroxamic acid) with 25 mg/kg/mouse or the compounds and the intermediates thereof as obtained in embodiments 1-7, the total proteins and the nucleoproteins were extracted with a total protein lysate and a nucleoprotein lysate (the total protein lysate, the nucleoprotein lysate and PMSF were purchased from Beyotime Biotechnology of Institute), 1 mg of tumor tissue was added into 1 ml of lysate, 10 μl of PMSF was added, dissociated repeatedly for uniform mixing, then the sample was placed on ice for 15 min, transferred into a 1.5 mL EP pipe, centrifuged at 14000 r/min and 4° C. for 10 min, and protein extract of the supernatant was transferred into the sterile EP pipe for detecting the enzyme activity.

(3) Observation of growth of tumors in nude mice: the activities (including food intake, traits of urine and stool, mental state and the like) of the nude mice and the tumor growth time and growth situation of the transplanted tumors were observed every day, the body weight and the size of the tumors were measured once every 2-3 days. The long diameter a and the short diameter b (mm) of each tumor were measured by a vernier caliper to calculate the volume, wherein the volume $V=\pi 1/2 \cdot ab^2$ (mm$^3$);

(4) sacrifice of animals: the mice were anesthetized and photoed after treatment experiments; the nude mice were sacrificed by breaking neck, the tumor tissues were stripped under sterile conditions and the weight of the tumors was weighed; and the effects of the drugs on pathology and toxicity of the various organs and tissues were detected.

(5) the weights of the transplanted tumors in the experimental groups were compared with the weights of the tumors (or lung metastases) in the blank control group to calculate the tumor inhibition rate, namely, the tumor inhibition rate (%)=(1−average tumor weight of the experimental group/average tumor weight of the control group)×100%.

3. Experimental results (see Table 2)

TABLE 2

Inhibitory effects of compounds and intermediates thereof as obtained in embodiments 1-7 on the in-vivo growth of a variety of human cancer xenografts in animal and mouse lung cancer metastasis

| Tumor type | Curative effect of tested compound § (inhibition rate %)* | | | | | | |
|---|---|---|---|---|---|---|---|
| | Compound Ia | Compound Ib | Compound Ic | Compound Id | Compound Ie | Compound If | Compound Ig |
| A549 | 48.6%* ± 5.9 | 53.6%* ± 5.5 | 61.6%* ± 5.5 | 63.6%* ± 6.3 | 55.5%* ± 6.9 | 58.6* ± 5.2 | 56.6%* ± 5.8 |
| MB-231 | 50.1%* ± 8.7 | 59.1%* ± 7.6 | 54.1%* ± 7.3 | 53.1%* ± 7.9 | 50.9%* ± 7.5 | 52.6* ± 7.1 | 59.1%* ± 7.8 |
| MCF-7 | 50.1%* ± 6.1 | 52.6%* ± 7.8 | 58.6%* ± 8.1 | 56.6%* ± 7.1 | 66.8%* ± 9.2 | 68.6%* ± 8.1 | 65.7%* ± 7.8 |
| S-7721 | 52.7% ± 11.5* | 60.8%* ± 8.9 | 63.2%* ± 8.6 | 67.2%* ± 8.6 | 64.8%* ± 9.3 | 65.7%* ± 8.6 | 53.6% ± 9.7* |
| PANC-1 | 55.8%* ± 7.9 | 54.6%* ± 8.3 | 56.5%* ± 8.6 | 54.2%* ± 9.6 | 56.6%* ± 9.9 | 53.6%* ± 9.7 | 55.6%* ± 9.3 |
| Hela | 54.7%* ± 8.8 | 53.9%* ± 9.1 | 53.7%* ± 8.6 | 57.9%* ± 9.5 | 60.7%* ± 9.9 | 50.9%* ± 8.5 | 56.7%* ± 8.9 |
| LLC | 55.4%* ± 9.8 # | 58.2%* ± 9.6 # | 74.2%* ± 9.1 # | 69.2%* ± 7. # | 61.6%* ± 8.5 # | 67.5%* ± 8.6 # | 75.5%* ± 13.6 # |

Inhibitory effects of compounds and intermediates thereof as obtained in embodiments 1-7 on the in-vivo growth of a variety of human cancer xenografts in animal and mouse lung cancer metastasis

| Tumor type | Curative effect of tested compound § (inhibition rate %)* | | | | |
|---|---|---|---|---|---|
| | Compound Ih | Compound IIb | Compound IIa | A/cisplatin B/CTX | ES | Ctrl |
| A549 | 53.8%* ± 6.7 | 33.3%* ± 6.3 | 29.6%* ± 6.9 | A/46.7% ± 6.5*; B/52.4% ± 6.9* | 38.9% ± 7.1* | ± − |
| MB-231 | 55.1%* ± 8.6 | 44.5%* ± 5.2 | 31.1%* ± 5.3 | A/61.3% ± 6.7*; B/.43.7% ± 7.9* | 33.5% ± 9.8* | − |
| MCF-7 | 58.9%* ± 7.9 | 43.2%* ± 7.6 | 39.8%* ± 7.9 | A.39.9%* ± 7.8; B.45.2%* ± 8.3 | 36.6%* ± 9.7 | − |
| S-7721 | 57.7% ± 8.9* | 44.6% ± 11.3* | 36.6% ± 11.1* | A.69.6%* ± 7.9; B.47.7%* ± 8.7 | 28.9%* ± 10.6 | ± − |
| PANC-1 | 51.3%* ± 9.8 | 32.3%* ± 12.5 | 33.4%* ± 11.3* | A/25.3%* ± 7.7 | 16.8%* ± 12.6 | − |
| Hela | 62.9%* ± 8.5 | 41.7%* ± 11.5 | 38.7%* ± 10.5 | A.36.6%* ± 7.5 | 17.2%* ± 11.8 | − |
| LLC | 77.9%* ± 13.1 # | 52.3%* ± 11.2 # | 36.8%* ± 8.9 | A/46.5%* ± 12.6 #; B/37.1%* ± 9.8 # | 42.7%* ± 13.8 # | − |

Note:
*$p < 0.05$; for the related test method, please see the above experimental method part;
§ inhibition rate % is the average inhibition rate (%) of the weights of the tumors of the medication group in comparison with that of the DMSO solvent control group; and
# is tumor lung metastasis inhibition rate % of mouse Lewis lung cancer.
A549: human lung cancer cells; MB231: MDA-MB231 (highly metastatic human breast cancer cells with negative estrogen receptor); MCF-7: estrogen receptor-positive human breast cancer cells; S-7721: SMMC7721 (human liver cancer cells); PANC-1: human pancreatic cancer cells; Hela: human cervical cancer cells; LLC: Lewis lung cancer (highly metastatic mouse lung cancer) cells; TMC: TMC group; TEC: TEC group; TCLC: TCLC group; TBrC: TBrC group; TFC: TFC group; TNC: TNC group; DTCLC; DTCLC group; DTBrC: DTBrC group; TE: TE group; TM: TM group; A: Cisplatin group; B: CTX group; ES: endostar group; and Ctrl: solvent control (DMSO).
Analysis results of animal pathology and toxicology showed that, during the experimental period, by treating the normal animals and the nude mice with the human cancer xenografts with all the synthetic components according to the dose of 60 mg/kg, no toxic and side effects were detected, no weight loss was observed, and no toxicity was found in heart, liver, spleen, lung, kidney, gastrointestinal tract, gonads, brain and skeletal muscles. In the positive control drug groups of cisplatin and cyclophosphamide, the mice had toxic reactions, represented by weight loss, anorexia, and abdominal swelling and slow actions and other phenomena after 2 weeks of medication. In the positive control groups of cisplatin, cyclophosphamide and endostar, the mice also had the toxicity phenomena of weight loss, anorexia, slow actions and the like.
The acute toxicity experimental results showed that, no death was found from oral administration of the synthetic components of the invention according to the dose of 2500 mg/kg.

TABLE 2-continued

Inhibitory effects of compounds and intermediates thereof as obtained in embodiments 1-7
on in-vivo growth of a variety of human cancer xenografts in animal and mouse lung cancer metastasis*

| Tumor type | Curative effect of tested compound § (inhibition rate %)* | | | | | | |
|---|---|---|---|---|---|---|---|
| | Compound Ia | Compound Ib | Compound Ic | Compound Id | Compound Ie | Compound If | Compound Ig |
| A549 | 51.6%* ± 9.9 | 60.6%* ± 9.5 | 67.6%* ± 5.5 | 69.6%* ± 6.3 | 61.5%* ± 8.9 | 64.6* ± 9.2 | 66.6%* ± 9.9 |
| MB-231 | 60.1%* ± 9.5 | 69.1%* ± 9.6 | 65.5%* ± 7.8 | 66.7%* ± 8.9 | 60.9%* ± 9.5 | 62.3* ± 9.8 | 72.1%* ± 9.8 |
| MCF-7 | 61.3%* ± 8.9 | 63.8%* ± 9.6 | 68.8%* ± 9.9 | 66.9%* ± 9.6 | 69.8%* ± 9.8 | 72.6%* ± 8.1 | 76.9%* ± 10.9 |
| S-7721 | 61.9% ± 10.8* | 66.6%* ± 9.7 | 69.2%* ± 9.6 | 75.7%* ± 9.5 | 69.9%* ± 9.6 | 75.7%* ± 10.8 | 70.6% ± 10.6* |
| PANC-1 | 60.5%* ± 9.3 | 65.9%* ± 9.6 | 66.7%* ± 9.3 | 64.8%* ± 9.9 | 64.6%* ± 9.3 | 67.3%* ± 10.5 | 68.9%* ± 11.9 |
| Hela | 62.9%* ± 9.6 | 63.8%* ± 10.5 | 65.8%* ± 9.8 | 71.9%* ± 10.7 | 70.5%* ± 9.3 | 66.8%* ± 9.8 | 70.3%* ± 9.6 |
| LLC | 60.9%* ± 10.6 # | 69.6%* ± 8.9 # | 79.2%* ± 9.6 # | 82.5%* ± 10.7 # | 70.8%* ± 9.3 # | 75.8%* ± 9.2 # | 79.9%* ± 12.3 # |

Inhibitory effects of compounds and intermediates thereof as obtained in embodiments 1-7
on in-vivo growth of a variety of human cancer xenografts in animal and mouse lung cancer metastasis*

| Tumor type | Curative effect of tested compound § (inhibition rate %)* | | | | | |
|---|---|---|---|---|---|---|
| | Compound Ih | Compound IIb | Compound IIa | A/cisplatin B/CTX | ES | Ctrl |
| A549 | 63.8%* ± 8.9 | 38.6%* ± 8.8 | 31.7%* ± 8.9 | A/46.7% ± 6.5*; B/52.4% ± 6.9* | 38.9% ± 7.1* | ± − |
| MB-231 | 75.1%* ± 9.3 | 47.8%* ± 9.2 | 36.1%* ± 8.8 | A/61.3% ± 6.7*; B/.43.7% ± 7.9* | 33.5% ± 9.8* | − |
| MCF-7 | 75.9%* ± 9.9 | 46.8%* ± 8.9 | 41.3%* ± 8.7 | A.39.9%* ± 7.8; B.45.2%* ± 8.3 | 36.6%* ± 9.7 | − |
| S-7721 | 78.7% ± 11.7* | 46.8% ± 10.9* | 38.2% ± 12.1* | A.69.6%* ± 7.9; B.47.7%* ± 8.7 | 28.9%* ± 10.6 | ± − |
| PANC-1 | 67.3%* ± 10.7 | 34.8%* ± 10.3 | 37.7% ± 10.7* | A/25.3%* ± 7.7 | 16.8%* ± 12.6 | − |
| Hela | 72.6%* ± 9.7 | 41.7%* ± 11.5 | 38.7%* ± 10.5 | A.36.6%* ± 7.5 | 17.2%* ± 11.8 | − |
| LLC | 80.7%* ± 12.8 # | 54.7%* ± 12.4 # | 38.5%* ± 10.7 | A/46.5%* ± 12.6 #: B/37.1%* ± 9.8 # | 42.7%* ± 13.8 # | − |

Note:
*p < 0.05; for the related test method, please see the above experimental method part;
§ inhibition rate % is the average inhibition rate (%) of the weights of the tumors of the medication group in comparison with that of the DMSO solvent control group; and
# is tumor lung metastasis inhibition rate % of mouse Lewis lung cancer.
A549: human lung cancer cells; MB231: MDA-MB231 (highly metastatic human breast cancer cells with negative estrogen receptor); MCF-7: estrogen receptor-positive human breast cancer cells; S-7721: SMMC7721 (human liver cancer cells); PANC-1: human pancreatic cancer cells; Hela: human cervical cancer cells; LLC: Lewis lung cancer (highly metastatic mouse lung cancer) cells; TMC: TMC group; TEC: TEC group; TCLC: TCLC group; TBrC: TBrC group; TFC: TFC group; TNC: TNC group; DTCLC: DTCLC group; DTBrC: DTBrC group; TE: TE group; TM: TM group: A: Cisplatin group; B: CTX group; ES: endostar group; and Ctrl: solvent control (DMSO).
Analysis results of animal pathology and toxicology showed that, during the experimental period, by treating the normal animals and the nude mice with the human cancer xenografts with all the synthetic compounds according to the dose of 90 mg/kg, no toxic and side effects were detected, no eight loss was observed, and no toxicity was found in heart, liver, spleen, lung, kidney, gastrointestinal tract, gonads, brain and skeletal muscles. In the positive control drug groups of cisplatin and cyclophosphamide, the mice had toxic reactions, represented by weight loss, anorexia, and abdominal swelling and slow actions and other phenomena were observed after 2 weeks of medication. In the positive control groups of cisplatin, cyclophosphamide and endostar, the mice also had the toxicity phenomena of weight loss, anorexia, slow actions and the like.
The acute toxicity experimental results showed that, no death was found from oral administration of all the synthetic components of the invention according to the dose of 2500 mg/kg.

Embodiment 10

Fluorescent Imaging of Compounds as Obtained in Embodiments 1-7

Fluorescent images and wavelength ranges of the compounds as obtained in embodiments 1-7 were determined according to the literature method (Chen Y, et al., 2-(3-{1-Carboxy-5-[(6-[18F]fluoro-pyridine-3-carbonyl)-amino]-pentyl}-ureido)-pentanedioic acid, [18F]DCFPyL, a PSMA-based PET imaging agent for prostate cancer. Clin Cancer Res, 2011, 17(24):7645-53), and the results were shown in Table 3 and FIG. 1.

1. Experimental animals, cell lines, main reagents and instruments: please refer to embodiment 9 in detail.
2. Experimental procedure: For in-vitro fluorescent imaging and detection: the compounds Ia-Ih as obtained in embodiments 1-7 were prepared in 1.5 ml plastic centrifugal tubes into a solution with the concentration of 60 mg/0.2 ml, fluorescent signals and images were respectively detected and recorded with a multifunctional microplate reader and an animal in-vivo imaging instrument under the following excitation and emission wavelength conditions, and the obtained results were shown in Table 3 and FIG. 1 (small test tube photos); and for the detection of fluorescent images in-vivo: after 16 h of fasting treatment of the experimental animals (while drinking water was normally supplied), solutions of the compounds Ia-Ih as obtained in embodiments 1-7 were prepared according to a concentration of 60 mg/kg body weight/0.2 ml, and intraperitoneally administered to the animal, the fluorescent images were detected and recorded with the animal in-vivo imaging instrument under the following excitation and emission wavelength conditions, the obtained results were shown in FIG. 1 (animal in-vivo imaged photos); wherein, the experimental excitation wavelength range was 360 nm-590 nm; and the detection wavelength range was 410 nm-700 nm.

3. Experimental results (see Table 3)

TABLE 3

Fluorescent images and wavelength ranges detectable in vivo and in vitro of compounds Ia-Ih as obtained in embodiments 1-7

| Compound and fluorescent wavelength | Compound Ia | Compound Ib | Compound Ic | Compound Id | Compound Ie | Compound If | Compound Ig | Compound Ih |
|---|---|---|---|---|---|---|---|---|
| Excitation nm | 360-610 | 360-610 | 360-610 | 36-610 | 360-610 | 360-610 | 360-610 | 360-610 |
| Emission nm | 430-650 | 430-650 | 430-670 | 430-670 | 430-650 | 430-650 | 430-690 | 430-690 |

Note:
experimental detection conditions: fluorescent images and wavelength ranges detectable in vivo and in vitro of compounds Ia-Ih as obtained in embodiments 1-7.
(1) Administration concentration: 60 mg/kg body weight/0.2 ml; and (2) excitation wavelength range: 360 nm-590 nm; and detectable wavelength range: 410 nm-690 nm.

Embodiment 11

Inhibitory Effects of Compounds Ia-Ih as Obtained in Embodiments 1-7 Against Activity of EZH2 Enzyme in Animals 1. Experimental animals, cell lines, instruments and main reagents Experimental animals: nude mice; and as for the cell lines and the instruments, please refer to the animal experimental part in embodiment 9 in detail.

EZH2 Assay Kit, purchased from BPS Bioscience Company.

The inhibitory effects of the compounds as obtained in embodiments 1-7 against the enzyme activity of EZH2 were detected, the experimental method was in strict accordance with the description of the kit for operation, and the steps were as follows:

2. Experimental procedure:

(1) 150 µl of TBST buffer solution was added into each reaction well of a microplate, incubated at room temperature for 15 min and the buffer solution was removed;

(2) S-adenosyl methionine and EZH2 enzyme working solutions were prepared according to the description and the operation was kept on an ice bath;

(3) a blank control product, a substrate control product, a positive control product, and an inhibitor control product were prepared according to the proportions indicated in the description;

(4) the various prepared control products and the samples to be tested (the EZH2 enzyme was replaced with tumor protein extracts in each group) were respectively added into the reaction wells according to 50 µl/well, reacted at room temperature for 1 h, and two parallel wells were set for each sample, wherein the method for obtaining the tumor protein extracts in each group was as described in the experiment procedure part of embodiment 9; the plate's washing and blocking: 200 µl of TBST buffer solution was added into each reaction well for washing the plate, and repeated for three times; and 100 µl of blocking buffer solution was further added into each reaction well, shaken on a shaking bed for blocking for 10 min, and the liquid was removed;

(5) a diluted primary antibody working solution was added into the reaction wells according to 100 µl/well and reacted on the shaking bed for 1 h;

(6) the plate was washed and blocked: the operation was the same as the operation (4);

(7) a diluted HRP-labeled secondary antibody working solution was added into the reaction wells according to 100 µl/well and reacted on the shaking bed for 30 min;

(8) the plate was washed and blocked: the operation was the same as the operation (4);

(9) equal volumes of HRP chemiluminescent substrates A and B were uniformly mixed on the ice bath and then added into the reaction wells according to 100 µl/well; and

(10) fluorescence values were immediately read on the microplate reader.

3. Experimental results (see Table 4)

TABLE 4

Effects of compounds Ia-Ih as obtained in embodiments 1-7 on in-vivo regulation of enzyme activity which was closely related to the growth, invasion and metastasis of tumors, cardiovascular and cerebrovascular diseases, immune deficiency, inflammation and the like Effective concentration
Effective doses for realizing regulatory effects and decrease or increase rates (%*) of compounds Ia-Ih as obtained in embodiments 1-7 against important enzyme activity related to tumors grown in vivo

| Enzyme activity | Compound Ia | Positive drug control (SAHA) | Compound Ib | Positive drug control (SAHA) | Compound Ic |
|---|---|---|---|---|---|
| decrease of EZH2 enzyme activity/ inhibition rate (%*) | 52%(LLC)-54%*(SMMC-7721) | 50%*(LLC-49%*(SMMC-7721); | 54%*(A549)-57%*(SMMC-7721) | 53%*(A549)-49%*(SMMC-7721); | 61%*(A549)-59%*(SMMC7721); 58%*(MDA-MB231) 56%*(MCF7) |
| decrease of HDAC3 and HDAC4 enzyme activity/ | 55%* and 52%*(LLC)-60%* and 58%*(SMMC7721) | 51%* and 49%*(LLC)-55%* and 57%*(SMMC-7721) | 65%* and 62%*(A549)-63%* and 61%*(SMMC-7721) | 63%* and 61%*(A549)-55%* and 57%*(SMMC-7721) | 71%* and 73%*(A549)-65%* and 67%*(SMMC7721); 63%* and |

TABLE 4-continued

Effects of compounds Ia-Ih as obtained in embodiments 1-7 on in-vivo regulation of enzyme activity which was closely related to the growth, invasion and metastasis of tumors, cardiovascular and cerebrovascular diseases, immune deficiency, inflammation and the like

| | | | | | |
|---|---|---|---|---|---|
| inhibition rate (%*) | | | | | 65%*(MDA-MB231) 60%* and 63%*(MCF7) |
| increase of H3 acetylation level (%*) | 56%* and 53%*(LLC)- 61%* and 63%*(SMMC7721) | 55%* and 52%*(LLC)- 60%* and 63%*(SMMC7721); | 66%* and 67%*(A549)- 63%* and 65%*(SMMC7721) | 63%* and 66%*(A549)- 60%* and 63%*(SMMC7721); | 75%* and 79%*(A549)- 73%* and 77%*(SMMC7721); 70%* and 72%*(MDA-MB231) 67%* and 69%*(MCF7) |
| increase of H4 acetylation level (%*) | 60%* and 63%*(LLC)- 65%* and 68%*(SMMC7721) | 55%* and 56%*(LLC)- 61%* and 64%*(SMMC7721) | 68%* and 69%*(A549)- 65%* and 68%*(SMMC7721) | 65%* and 67%*(A549)- 61%* and 64%*(SMMC7721) | 78%* and 80%*(A549)- 75%* and 78%*(SMMC7721); 72%* and 75%*(MDA-MB231) 70%* and 73%*(MCF7) |

Effective concentration
Effective doses for realizing regulatory effects and decrease or increase rates (%*) of compounds Ia-Ih as obtained in embodiments 1-7 against important enzyme activity related to tumors grown in vivo

| Enzyme activity | Positive drug control (SAHA) | Compound Id | Positive drug control (SAHA) | Solvent control |
|---|---|---|---|---|
| decrease of EZH2 enzyme activity/ inhibition rate (%*) | 53%*(A549); 49%*(SMMC7721); 55%*(MDA-MB231) 53%*(MCF7) | 61%*(A549)- 59%*(SMMC7721); 58%*(MDA-MB231) 56%*(MCF7) | 53%*(A549)- 49%*(SMMC7721); 55%*(MDA-MB231) 53%*(MCF7) | – |
| decrease of HDAC3 and HDAC4 enzyme activity/ inhibition rate (%*) | 63%* and 61%*(A549)- 55%* and 57%*(SMMC7721) 56%* and 59%*(MDA-MB231) 53%* and 56%*(MCF7) | 71%* and 73%*(A549)- 65%* and 67%*(SMMC7721); 63%* and 65%*(MDA-MB231) 60%* and 63%*(MCF7) | 63%* and 61%*(A549)- 55%* and 57%*(SMMC7721); 56%* and 59%*(MDA-MB231) 53%* and 56%*(MCF7) | – |
| increase of H3 acetylation level (%*) | 63%* and 66%*(A549)- 60%* and 63%*(SMMC7721); 57%* and 60%*(MDA-MB231) 55%* and 58%*(MCF7) | 75%* and 79%*(A549)- 73%* and 77%*(SMMC7721); 70%* and 72%*(MDA-MB231) 67%* and 69%*(MCF7) | 63%* and 66%*(A549)- 60%* and 63%*(SMMC7721); 57%* and 60%*(MDA-MB231) 55%* and 58%*(MCF7) | – |
| increase of H4 acetylation level (%*) | 65%* and 67%*(A549)- 61%* and 64%**(SMMC7721); 57%* and 62%*(MDA-MB231) 58%* and 62%*(MCF7) | 78%* and 80%**(A549)- 75%* and 78%*(SMMC7721); 72%* and 75%*(MDA-MB231) 70%* and 73%*(MCF7) | 65%* and 67%*(A549)- 61%* and 64%*(SMMC7721); 57%* and 62%*(MDA-MB231) 58%* and 62%*(MCF7) | – |

Effective concentration

| Enzyme activity | Compound Ie | Positive drug control (SAHA) | Compound If | Positive drug control (SAHA) |
|---|---|---|---|---|
| decrease of EZH2 enzyme activity/ inhibition rate (%*) | 58%*(A549)- 56%*(SMMC7721); 59%*(MDA-MB231) 62%*(MCF7) | 53%*(A549)- 49%*(SMMC7721); 55%*(MDA-MB231) 53%*(MCF7) | 65%*(A549)- 64%*(SMMC7721); 63%*(MDA-MB231) 66%*(MCF7) | 53%*(A549)- 49%*(SMMC7721); 55%*(MDA-MB231) 53%*(MCF7) |
| decrease of HDAC3 and HDAC4 enzyme activity/ | 70%* and 72%*(A549)- 63%* and 65%*(SMMC7721); 60%* and | 63%* and 61%*(A549)- 55%* and 57%*(SMMC7721); 56%* and | 73%* and 75%*(A549)- 66%* and 68%*(SMMC7721); 65%* and | 63%* and 61%*(A549)- 55%* and 57%*(SMMC7721); 56%* and |

TABLE 4-continued

Effects of compounds Ia-Ih as obtained in embodiments 1-7 on in-vivo regulation of enzyme activity which was closely related to the growth, invasion and metastasis of tumors, cardiovascular and cerebrovascular diseases, immune deficiency, inflammation and the like

| inhibition rate (%*) | 62%*(MDA-MB231) 65%* and 67%*(MCF7) | 59%*(MDA-MB231) 53%* and 56%*(MCF7) | 67%*(MDA-MB231) 67%* and 69%*(MCF7) | 59%*(MDA-MB231) 53%* and 56%*(MCF7) |
|---|---|---|---|---|
| increase of H3 acetylation level (%*) | 73%* and 76%*(A549)- 71%* and 74%*(SMMC7721); 72%* and 75%*(MDA-MB231) 69%* and 71%*(MCF7) | 63%* and 66%*(A549)- 60%* and 63%*(SMMC7721); 57%* and 60%*(MDA-MB231) 55%* and 58%*(MCF7) | 76%* and 79%*(A549)- 75%* and 78%*(SMMC7721); 73%* and 75%*(MDA-MB231) 71%* and 73%*(MCF7) | 63%* and 66%*(A549)- 60%* and 63%*(SMMC7721); 57%* and 60%*(MDA-MB231) 55%* and 58%*(MCF7) |
| increase of H4 acetylation level (%*) | 75%* and 77%*(A549)- 71%* and 73%*(SMMC7721); 73%* and 76%*(MDA-MB231) 75%* and 77%(MCF7) | 65%* and 67%*(A549)- 61%* and 64%*(SMMC7721); 57%* and 62%*(MDA-MB231) 58%* and 62%(MCF7) | 77%* and 80%*(A549)- 76%* and 78%*(SMMC7721); 73%* and 74%*(MDA-MB231) 74%* and 76%*(MCF7) | 65%* and 67%*(A549)- 61%* and 64%*(SMMC7721); 57%* and 62%*(MDA-MB231) 58%* and 62%(MCF7) |

| | Effective concentration | | | |
|---|---|---|---|---|
| Enzyme activity | Compound Ig | Compound Ih | Positive drug control (SAHA) | Solvent control |
| decrease of EZH2 enzyme activity/ inhibition rate (%*) | 57%*(A549)- 58%*(SMMC7721); 61%*(MDA-MB231) 65%*(MCF7) | 55%*(A549)- 56%*(SMMC7721); 59%*(MDA-MB231) 61%*(MCF7) | 52%(A549); 48%*(SMMC7721); 54%*(MDA-MB231) 52%*(MCF7) | – |
| decrease of HDAC3 and HDAC4 enzyme activity/ inhibition rate (%*) | 61%* and 63%*(A549)- 62%* and 64%*(SMMC7721); 64%* and 66%*(MDA-MB231) 66%* and 68%*(MCF7) | 57%* and 59%*(A549)- 60%* and 62%*(SMMC7721); 62%* and 64%*(MDA-MB231) 64%* and 66%*(MCF7) | 62%* and 60%*(A549)- 54%* and 56%*(SMMC7721); 55%* and 58%*(MDA-MB231) 52%* and 55%*(MCF7) | – |
| increase of H3 acetylation level (%*) | 65%* and 67%*(A549)- 66%* and 68%*(SMMC7721); 69%* and 71%*(MDA-MB231) 72%* and 74%*(MCF7) | 64%* and 66%*(A549)- 65%* and 67%*(SMMC7721); 67%* and 69%*(MDA-MB231) 68%* and 70%*(MCF7) | 61%* and 63%*(A549)- 61%* and 63%*(SMMC7721); 58%* and 60%*(MDA-MB231) 54%* and 56%*(MCF7) | – |
| increase of H4 acetylation level (%*) | 72%* and 74%*(A549)- 73%* and 75%*(SMMC7721); 74%* and 76%*(MDA-MB231) 76%* and 78%(MCF7) | 70%* and 72%*(A549)- 71%* and 73%*(SMMC7721); 72%* and 74%*(MDA-MB231) 73%* and 75%(MCF7) | 64%* and 66%*(A549)- 60%* and 62%**(SMMC7721); 56%* and 60%*(MDA-MB231) 57%* and 59%(MCF7) | – |

Note:
*p < 0.05; and as for the related test method, please see the above experimental method part. The H3 and H4 acetylation levels (%) were obtained by analysis of LLC (highly metastatic Lewis mouse lung cancer) through Western Blotting; and the method was as described in detail in the related part contents in the following embodiments 12-13.

Embodiment 12

Inhibitory Effects of Compounds Ia-Ih as Obtained in Embodiments 1-7 Against Activity of Histone Methyltransferase (HDAC)

1. Experimental animals, cell lines, instruments and main reagents

Experimental animals: nude mice; and as for the cell lines and the instruments, please refer to the animal experimental part in embodiment 9 in detail.

EpiQuik HDAC Activity/Inhibition Assay Kit (Colorimetric): Epigentek Company;

EpiQuik Nuclear Extraction Kit, Epigentek Company;

2. Experimental procedure (1) tumor nuclear extracts after drug treatment were prepared in strict accordance with the operation requirements of description of EpiQuik Nuclear Extraction Kit (see the experimental procedure part of embodiment 9); and two parallel wells were set for each sample;

(2) 50 μl of diluted sample solution was added into each reaction well, the plate was sealed with a plate-sealing film and reacted at room temperature for 30 min;

(3) the plate-sealing film was carefully peeled off, the liquid was removed, dried, 150 µl of washing liquid was added into each well, stood for 30 s, then the liquid was removed, repeated twice, and dried;

(4) 2 µl of HDAC enzyme or tumor tissue nuclear extracts was respectively uniformly mixed with 28 µl of diluted sample solution, added into the wells, the plate was sealed with the plate-sealing film and reacted at 37° C. for 60 min;

(5) the plate was washed for three times, wherein the operation was the same as that in (3); and a diluted antibody capture working solution was added into each reaction well according to 50 µl/well and reacted on a shaking bed at room temperature for 60 min;

(6) the plate was washed for four times, wherein the operation was the same as that in (3);

(7) a diluted antibody detection working solution was added into each reaction well according to 50 µl/well and reacted at room temperature for 30 min;

(8) the plate was washed for five times, wherein the operation was the same as that in (3);

a color developing agent was added according to 100 µl/well, and performed dark development for 2-10 min;

(9) 50 µl of stop solution was added into each well for stopping the reaction when the color in the well with a standard product turned blue with medium intensity, the color immediately turned yellow from blue after the addition;

(10) the light absorbance (OD value) of each well was measured in sequence at the wavelength of 450 nm; wherein the measurement should be performed within 15 min after addition of the stop solution; and

(12) the enzyme activity inhibition rate was calculated according to the following formula:

Inhibitory rate %=[1−(OD of positive control−OD of sample)/(OD of positive control−OD of blank control)]100%

3. Experimental results (see Table 4)

Embodiment 13

Experiments on Effects of Compounds Ia-Ih as Obtained in Embodiments 1-7 in Regulating the Level of Protein Factors which were Closely Related to the Growth, Invasion and Metastasis of a Variety of Tumors, Cardiovascular Diseases, Immune Deficiency, Inflammation and the Like A Western Blotting method was applied to detect the effects of the compounds Ia-Ih as obtained in embodiments 1-7 in regulating the level of the protein factors which were related to the following tumors, and the procedure was as follows:

1. Main Reagents and Instruments:

Antibodies: primary antibodies of VEGFR, EGFR, c-Met, K-Ras, H-Ras, Akt, NF-κB, Cyclin D1, ER-alpha, Dvl-1, Dvl-2, Dvl-3, MMP-9, MMP2, β-catenin, Bcl-2, Bax, p53, p21, E-cadherin and Caspase3 protein, purchased from American Cell Signaling Technology Company and Santa Cruz Technology Company; and H3 acetylation, H4 acetylation and HDAC (HDAC3, HDAC4 and the like) Antibody Sample Kits, purchased from Cell Signaling Technology Company of the U.S.

RPMI-1640, DMEM culture solutions and inactivated fetal calf serum: purchased from Hyclone Company; trypsin: purchased from Amersco Company; protein molecular Marker and 0.4% trypan blue: purchased from Sigma Company of the U.S.; and PVDF film: purchased from Millipore Company;

total protein lysate, nucleoprotein lysate and PMSF (phenylmethylsulfonyl fluoride) solutions: purchased from Beyotime Biotechnology of Institute; secondary antibodies: horse radish peroxidase-labeled goat anti-mouse antibody, horse radish peroxidase labeled goat anti-rabbit antibody, horse radish peroxidase-labeled donkey anti-goat antibody, a color prestained protein molecular weight marker, an ECL Plus luminescent kit, fixing powder, and developing powder: purchased from Beyotime Biotechnology of Institute; and a medical X-ray film: purchased from Kodak Company.

A carbon dioxide incubator: 3111, Thermo Company of the U.S.; an inverted microscope: CKX31, Olympus Company of Japan; a table type high-speed refrigerated centrifuge: 5810R, Eppendorf Company of Germany; micropipettes: Eppendorf Company of Germany; a cell culture plastic plate (6-well): Nunclon company; a small vertical electrophoresis tank: BIO-RAD Company of the U.S.; a small wet electrical transfer tank: BIO-RAD Company of the U.S.; a decolorization shaking bed: TS-1 type, Jiangsu Haimen Kylin-Bell Lab Instruments Co., Ltd.; an ice making machine: XB 70, GRANT Company; an OMEGA10 gel imaging analyzer:µlTRA LUM Company of the U.S.; a sealing machine: SF-B, Wenzhou Xingye Machinery Co., Ltd.; a protein analysis lightbox: Shanghai Jingke Industrial Co., Ltd.

2. Experimental Procedure:

(1) Cell treatment: cells in a logarithmic growth phase were inoculated into a 6-well plate, the detected compounds Ia-Ih as obtained in embodiments 1-7 and positive control drugs cyclophosphamide and the like were respectively added into the cells when the density of the cells were about 70%-80% to enable the final concentration to be 1-1500 µM/L respectively, a control group with the equal volume of the cell culture solution, which did not contain a drug but a solvent (0.01% DMSO), was set, continuously cultured for 48 h and then the cells were collected;

(2) extraction of cell proteins: after washed with cold PBS twice, the cells were lysed with the total protein or nucleoprotein lysate, 10 µl of PMSF was added into 1 mL of lysate, repeatedly dissociated for uniformly mixing and placed on ice for 15 min; and the sample was transferred into a 1.5 mL EP pipe, centrifuged at 14000 r/min and 4° C. for 10 min, the supernatant was transferred into a sterile EP pipe and preserved at −80° C.; and (3) polyacrylamide gel electrophoresis (SDS-PAGE): an equal amount of protein lysate sample was used to separate protein, film transfer, and blocking, treated with appropriate primary antibodies and secondary antibodies in sequence, and the film was washed, then the color was developed with ECL kit, and a blot protein band was detected by exposure of an X-ray film; and a Gel-Pro Analyzer was used for quantitative analysis of gray degree, optical density value of the control group and the drug treatment group in various concentration were respectively compared with that of internal reference, the obtained ratios were respectively compared with the control group, and the protein expression level was semi-quantified.

3. Experimental results (see Table 5 and Table 6)

TABLE 5

Effects of compounds Ia-Ih as obtained in embodiments 1-7 in inhibition of protein factors which were closely related to the growth, invasion and metastasis of tumors, cardiovascular and cerebrovascular diseases, immune deficiency, inflammation and the like

| Protein or enzyme | Effective concentration (mM/L) | | | | | |
|---|---|---|---|---|---|---|
| | Compound Ia | Compound Ib | Compound Ic | Compound Id | Positive drug control | Blank control (Solvent) |
| Bcl-2/Bax | <0.125 * | <0.12 * | <0.1 * | <0.1 * | >1.0 * | — |
| Cyclin D1 | <0.125 * | <0.12 * | <0.1 * | <0.1 * | >1.0 * | — |
| Akt | <0.125 * | <0.12 * | <0.1 * | <0.1 * | >1.0 * | — |
| K-Ras | <0.085 * | <0.075 * | <0.065 * | <0.06 * | >1.0 * | — |
| H-Ras | <0.085 * | <0.075 * | <0.065 * | <0.06 * | >1.0 * | — |
| NF-κB | <0.125 * | <0.12 * | <0.1 * | <0.08 * | >1.0 * | — |
| NF-κB-DNA binding activity | <0.135 * | <0.13 * | <0.125 * | <0.12 * | >1.0 * | — |
| Nuclear β-catenin | <0.12 * | <0.12 * | <0.1 * | <0.1 * | >1.0 * | — |
| Dvl-1 | <0.135 * | <0.30 * | <0.25 * | <0.25 * | >1.0 * | — |
| VEGFR1 | <0.125 * | <0.12 * | <0.1 * | <0.1 * | >1.0 * | — |
| VEGFR2 | <0.125 * | <0.12 * | <0.1 * | <0.1 * | >1.0 * | — |
| EGFR | <0.125 * | <0.12 * | <0.1 * | <0.1 * | >1.0 * | — |
| c-Met | <0.16 * | <0.155 * | <0.5 * | <0.15 * | >1.0 * | — |
| HDAC3 | <0.075 * | <0.07 * | <0.065 * | <0.065 * | >0.5 * | — |
| HDAC4 | <0.065 * | <0.06 * | <0.05 * | <0.05 * | >0.5 * | — |

Effective concentration (mM/L)
Effective concentrations (IC50) of compounds Ia-Ih as obtained in embodiments 1-7 for inhibition of related important signal transduction pathway receptors, regulatory proteins and kinases

| Protein or enzyme | Compound Ie | Compound If | Positive drug control (endostar, cyclophosphamide) | Blank control (Solvent) |
|---|---|---|---|---|
| Bcl-2/Bax | <0.18 * | <0.09 * | >0.25 * | — |
| Cyclin D1 | <0.16 * | <0.09 * | >0.25 * | — |
| Akt | <0.16 * | <0.09 * | >0.25 * | — |
| K-Ras | <0.06 * | <0.055 * | >0.25 * | — |
| H-Ras | <0.06 * | <0.055 * | >0.25 * | — |
| NF-κB | <0.06 * | <0.06 * | >0.25 * | — |
| NF-κB-DNA binding activity | <0.1 * | <0.10 * | >0.25 * | — |
| Nuclear β-catenin | <0.065 * | <0.09 * | >0.25 * | — |
| Dvl-1 | <0.15 * | <0.20 * | >0.25 * | — |
| VEGFR1 | <0.11 * | <0.09 * | >0.25 * | — |
| VEGFR2 | <0.09 * | <0.09 * | >0.25 * | — |
| EGFR | <0.11 * | <0.1 * | >0.25 * | — |
| c-Met | <0.145 * | <0.141 * | >0.25 * | — |
| HDAC3 | <0.055 * | <0.055 * | >0.25 * | — |
| HDAC4 | <0.05 * | <0.045 * | >0.25 * | — |

Effective concentration (mM/L)
Effective concentrations (IC50) of compounds and intermediates thereof as obtained in embodiments 1-7 for inhibition of related important signal transduction pathway receptors, regulatory proteins and kinases

| Protein or enzyme | Compound Ig | Compound Ih | Positive drug control (Endostar) | Blank control (solvent) |
|---|---|---|---|---|
| Bcl-2/Bax | <0.07 * | <0.07 * | >500 mg/L * | — |
| Cyclin D1 | <0.07 * | <0.07 * | >500 mg/L | — |
| Akt | <0.07 * | <0.07 * | >500 mg/L * | — |
| K-Ras | <0.065 * | <0.065 * | >500 mg/L * | — |
| H-Ras | <0.065 * | <0.065 * | >500 mg/L * | — |
| NF-κB | <0.1 * | <0.1 * | >500 mg/L * | — |
| NF-κB-DNA binding activity | <0.125 * | <0.125 * | >500 mg/L * | — |
| Nuclear β-catenin | <0.1 * | <0.1 * | >500 mg/L * | — |
| Dvl-1 | <0.125 * | <0.25 * | >500 mg/L * | — |
| VEGFR1 | <0.1 * | <0.1 * | >250 mg/L * | — |
| VEGFR2 | <0.1 * | <0.1 * | >250 mg/L * | — |
| EGFR | <0.1 * | <0.1 * | >500 mg/L * | — |
| c-Met | <0.15 * | <0.5 * | >500 mg/L * | — |
| HDAC3 | <0.065 * | <0.065 * | >500 mg/L * | — |

TABLE 5-continued

Effects of compounds Ia-Ih as obtained in embodiments 1-7 in inhibition of protein factors which were closely related to the growth, invasion and metastasis of tumors, cardiovascular and cerebrovascular diseases, immune deficiency, inflammation and the like

| | | | | |
|---|---|---|---|---|
| HDAC4 | <0.05 * | <0.05 * | >500 mg/L * | – |
| Dvl-2 | <0.1 * | <0.1 * | >250 mg/L * | – |
| DVl-3 | <0.1 * | <0.1 * | >250 mg/L * | – |
| ER-alpha | <0.1 * | <0.1 * | >250 mg/L * | – |
| MMP9 | <0.065 * | <0.065 * | >250 mg/L * | – |
| MMP2 | <0.05 * | <0.05 * | >250 mg/L * | – |

Note:
$p < 0.05$; and as for the related test method, please see the above experimental method part.

The related protein factors in the table were all from human liver cancer cells, Lewis lung cancer cells and other cancer cell lines and protein lysates of these tumor tissues, which were treated by the compounds Ia-Ih as obtained in embodiments 1-7 or the positive control anti-cancer drugs or the DMSO solvent, the results were given by detection and analysis with Western blotting.

TABLE 6

Effects of compounds Ia-Ih as obtained in embodiments 1-7 on protein factor level and enzyme activity which were closely related to the growth, invasion and metastasis of tumors, cardiovascular and cerebrovascular diseases, immune deficiency, inflammation and the like Effective concentration
Effective concentrations (mM/L) of compounds Ia-Ih as obtained in embodiments 1-7 for regulation of expression level of related important regulatory proteins and enzyme activity

| Protein or enzyme | Compound Ia | Compound Ib | Compound Ic | Compound Id | Positive drug control | Blank control (Solvent) |
|---|---|---|---|---|---|---|
| Increase p53 by 50% | <0.125 * | <0.12 * | <0.1 * | <0.1 * | >1.5 * | – |
| Increase p21 by 50% | <0.125 * | <0.12 * | <0.1 * | <0.1 * | >1.5 * | – |
| Increase Caspase-3 by 50% | <0.125 * | <0.12 * | <0.1 * | <0.1 * | >1.5 * | – |
| Increase cytoplasma/mitochondrial cytochrome C ratio by 50% | <0.075 * | <0.07 * | <0.065 * | <0.065 * | >1.0 * | – |
| Increase E-cadherin by 50% | <0.075 * | <0.07 * | <0.065 * | <0.065 * | >1.0 * | – |

Effective concentration
Effective concentrations (mM/L) of compounds Ia-Ih as obtained in embodiments 1-7 for regulation of expression level of related important regulatory proteins and enzyme activity

| Protein or enzyme | Compound Ie | Compound If | Positive drug control (endostar, cyclophosphamide) | Blank control (Solvent) |
|---|---|---|---|---|
| Increase p53 by 50% * | <0.1 * | <0.065 * | >0.25 * | – |
| Increase p21 by 50% * | <0.1 * | <0.065 * | >0.25 * | – |
| Increase Caspase-3 by 50% * | <0.1 * | <0.08 * | >0.25 * | – |
| Increase cytoplasma/mitochondrial cytochrome C ratio by 50% * | <0.065 * | <0.065 * | >0.25 * | – |
| Increase E-cadherin by 50% * | <0.065 * | <0.065 * | >0.25 * | – |

Effective concentration
Effective concentrations (IC50) (mM/L) of compounds Ia-Ih as obtained in embodiments 1-7 for regulatory effect on expression level of related important regulatory proteins and enzyme activity

| Protein or enzyme | Compound Ig | Compound Ih | Positive drug control (Vincristine) | Blank control (Solvent) |
|---|---|---|---|---|
| Increase p53 by 50% | <0.07 * | <0.07 * | >0.07 * | – |
| Increase p21 by 50% | <0.07 * | <0.1 * | >0.07 | – |
| Increase Caspase-3 by 50% | <0.07 * | <0.07 * | >0.07 | – |

TABLE 6-continued

Effects of compounds Ia-Ih as obtained in embodiments 1-7 on protein factor level and enzyme activity which were closely related to the growth, invasion and metastasis of tumors, cardiovascular and cerebrovascular diseases, immune deficiency, inflammation and the like

| | | | | |
|---|---|---|---|---|
| Increase cytoplasma/mitochondrial cytochrome C ratio by 50% | <0.07 * | <0.07 * | >0.07 * | — |
| Increase E-cadherin by 50% | <0.07 * | <0.07 * | >0.07 * | — |

Note:
* $p < 0.05$; as for the related test method, please see the above experimental method part.
: The results of the related tumor suppressor protein p53, cell cycle inhibitory protein p21, cell apoptosis hydrolase Caspase-3, cytoplasma/mitochondrial cytochrome C ratio, and cell adhesion protein E-cadherin were all the detection and analysis results with Western blotting of liver cancer cells, Lewis lung cancer cells and other cancer cell lines and protein lysates of these tumor tissues, which were treated by the compounds Ia-Ih as obtained in embodiments 1-7 or the positive control anti-cancer drugs or the DMSO solvent.

Embodiment 14

In-Vitro Experiments of Inhibitory Effects of Compounds Ia-Ih as Obtained in Embodiments 1-7 Against Nucleoprotein Factor NF-κB (p65)-DNA Binding Activity (EMSA)

Main Reagents and Instruments:

A chemiluminescent EMSA kit: Pierce Biotechnology Company of the U.S.;

A biotin-labeled EMSA probe NF-κB: Pierce Biotechnology Company of the U.S.;

Protein molecular Marker and 0.4% trypan blue: Sigma Company of the U.S.; a PVDF film: Millipore Company;

A nucleoprotein lysate and a PMSF (phenylmethylsulfonyl fluoride) solution: Beyotime Biotechnology of Institute;

a color prestained protein molecular weight marker, an ECL Plus luminescent kit, fixing powder and developing powder: Beyotime Biotechnology of Institute. A medical X-ray film: Kodak Company.

Experimental Procedure:

The cancer cells were treated with 1-500 μM/L of compounds Ia-Ih as obtained in embodiments 1-7 and 0.1-1000 μM/L of vincristine and DMSO (0.01%) for 48 h to obtain cell nuclear protein extracts, wherein the method was as described in detail in experimental part of embodiment 6. The in-vitro experiment of the inhibitory effect against the NF-κB(p65)-DNA binding activity was applied with the chemiluminescent EMSA kit of Pierce Biotechnology Company of the U.S., the experimental method was strictly operated according to the description of the kit and the specific procedure were as follows:

(1) Preparation of EMSA gel

The preparation of the EMSA gel was shown in the following table. The cells treated by the drugs were extracted by the nucleoprotein extract solution (provided by Beyotime Biotechnology of Institute) to obtain the nucleoprotein extracts, and 10 μg/pipe of the nucleoprotein extracts were respectively used for sample reaction and electrophoresis detection and analysis shown in the following table.

TABLE 7-1

Preparation of 4%* polyacrylamide gel

| Name of component | Loading volume of sample |
|---|---|
| TBE buffer (10X) | 1.0 ml |
| Redistilled water | 16.2 ml |
| 39:1 Acrylamide | 2 ml |
| 80% glycerol | 625 μl |
| 10% ammonium persufate | 150 μl |
| TEMED | 10 μl |

(2) Pre-electrophoresis: the gel was fixed in an electrophoresis tank, which was filled with a 0.5×TBE electrophoresis buffer solution, and electrophoresed under 10V/cm for 90 min. The probe binding reaction was as follows:

TABLE 7-2

Negative control reaction

| Name of component | Volume |
|---|---|
| Nuclease-Free Water | 7 μl |
| EMSA/Gel-Shift binding buffer solution (5X) | 2 μl |
| Cell nucleoproteins or purified transcription factors | 0 μl |
| Labeled probe | 1 μl |
| Total volume | 10 μl |

TABLE 7-3

Sample reaction

| Name of component | Volume |
|---|---|
| Nuclease-Free Water | 0 μl |
| EMSA/Gel-Shift binding buffer solution (5X) | 2 μl |
| Cell nucleoproteins or purified transcription factors | 7 μl |
| Labeled probe | 1 μl |
| Total volume | 10 μl |

The components were added in sequence into the EP pipe according to the above table, uniformly mixed and stood at room temperature for 15 min to eliminate possible non-specific binding of probe and protein. 1 μl of biotin-labeled probe NF-κB was respectively added and stood at room temperature for 20 min.

(3) Electrophoresis: replaced with the fresh 0.5×TBE electrophoresis buffer solution, electrophoresed under 10V/cm for 1.5 h and ensured that the temperature of the gel did not exceed 30° C.

(4) Film transfer: the process of transferring the nucleoprotein factors and the binding probe on the EMSA gel to the nylon film was electrically transferred under 380 mA in ice bath for 40 min.

(5) Ultraviolet cross-linking: the nylon film was placed under a 254 nm ultraviolet lamp and irradiated for 15 min.

(6) Detection of the biotin-labeled probe by chemiluminescence: the cross-linked nylon film was blocked with the blocking solution, a treated film was subjected to X-ray exposure, developing, and fixation according to the requirements of the kit, and the results were analyzed.

3. Experimental Results

Additional remarks: the application of the patent and the research work related to the results are funded by National 863 program "Research and development of tumor protein molecular markers (2012AA020206)" and Shandong Province Science and Technology Development Plan Project "Structural transformation and optimization of ester catechins (EGCG) and other active components and research of new anti-cancer candidate drugs (2009GG10002087)", as well as Natural Science Foundation Project of Shandong Province (ZR2012HM016).

TABLE 8

Inhibitory effects of compounds Ia-Ih as obtained in embodiments 1-7 on nucleoprotein factor NF-$_k$B (p65) which was closely related to the growth, invasion and metastasis of tumors, cardiovascular and cerebrovascular diseases, immune deficiency, inflammation and the like, and DNA activity (cells and tumor tissue nuclearprotein)

| | Effective concentration Effective concentrations of compounds Ia-Ih as obtained in embodiments 1-7 for 50% inhibition of binding of nucleoprotein factor NF-$_k$B (p65) and DNA * | | | | | | | |
|---|---|---|---|---|---|---|---|---|
| Inhibition rate (%) | Compound Ia | Compound Ib | Compound Ic§ | Compound Id | Compound Ie | Compound If | Positive drug control§ | Solvent control |
| 50% inhibition of A549 cells | | <0.135 * | <0.125 * | <0.11 * | <0.12 | <0.10 * | >1.0 * | — |
| 50% inhibition of SMMC7721 cells | <0.125 * | <0.12 * | <0.125 * | <0.08 ** | <0.121 | <0.10 * | >1.0 * | — |
| 50% inhibition of MDA-MB231 cells | | | <0.125 * | <0.1 * | <0.11 | <0.10 * | >1.0 * | — |
| 50% inhibition of MCF7 cells | | | <0.125 ** | <0.1 * | <0.10 | <0.10 * | >1.0 * | — |
| 50% inhibition of Lewis lung cancer cells | <0.135 * | | | | | | | |

| | Effective concentration Effective concentrations of compounds Ia-Ih as obtained in embodiments 1-7 for 50% inhibition of binding of nucleoprotein factor NF-$_k$B (p65) and DNA | | | |
|---|---|---|---|---|
| Inhibition rate (%) | Compound Ig§ | Compound Ih§ | Positive drug control§ (vincristine) | Blank control (solvent) |
| 50% inhibition of A549 cells | <0.07 * | <0.07 * | >0.07 * | — |
| 50% inhibition of SMMC7721 cells | <0.07 * | <0.07 * | >0.07 * | — |
| 50% inhibition of MDA-MB231 cells | <0.07 * | <0.07 * | >0.07 * | — |
| 50% inhibition of MCF7 cells | <0.07 * | <0.07 * | >0.07 * | — |
| 50% inhibition of PANC-1 cells | <0.07 * | <0.07 * | >0.07 * | — |
| 50% inhibition of Hela cells | <0.07 * | <0.07 * | >0.07 * | — |

§When the in-vivo tumor tissue nucleoprotein lysate was used for detection, the amount of the compounds as obtained in embodiments 1-7 and the cyclophosphamide for intraperitoneal injection was 60 mg/kg and 25 mg/kg respectively.

What is claimed is:

1. A compound as represented by formula (I):

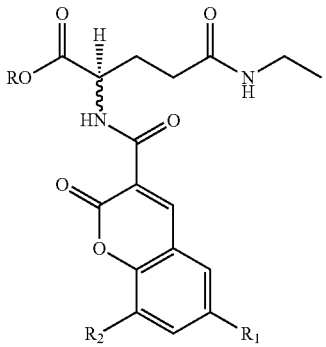

Formula (I)

wherein Formula (I) has variables and bonds selected from (Ib) to (Ii), wherein;
R=CH$_2$CH$_3$, and (Ib) R$_1$=H, R$_2$=H and ⁓⁓⁓ = ·····⫿⫿⫿⫿ ;
(Ic) R$_1$=Cl, R$_2$=H and ⁓⁓⁓ = ◄━━ ;
(Id) R$_1$=Br, R$_2$=H and ⁓⁓⁓ = ◄━━ ;
(Ie) R$_1$=F, R$_2$=H and ⁓⁓⁓ = ·····⫿⫿⫿⫿ ;
(If) R$_1$=NO$_2$, R$_2$=H and ⁓⁓⁓ = ·····⫿⫿⫿⫿ ;
(Ig) R$_1$=Cl, R$_2$=Cl and ⁓⁓⁓ = ◄━━ ;
(Ih) R$_1$=Br, R$_2$=Br and ⁓⁓⁓ = ◄━━ ; or
(Ii) R$_1$=NH$_2$, R$_2$=H and ⁓⁓⁓ = ·····⫿⫿⫿⫿ .

2. A method for preparing a compound as represented by formula (I):

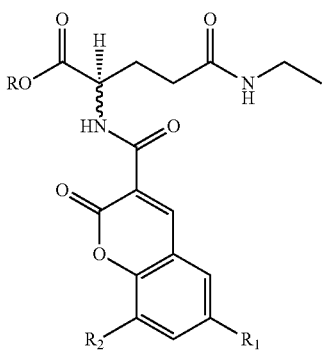

Formula (I)

wherein
R=CH$_2$CH$_3$, and
R$_1$=H, R$_2$=H and ⁓⁓⁓ = ·····⫿⫿⫿⫿ ;
comprising:

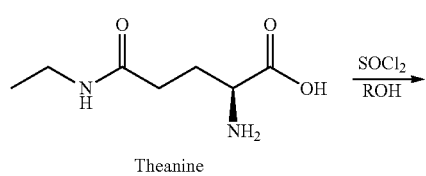

Theanine

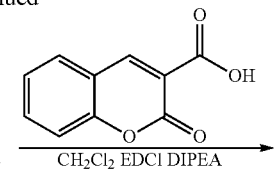

(IIa) R = CH3
(IIb) R = CH2CH3 wherein

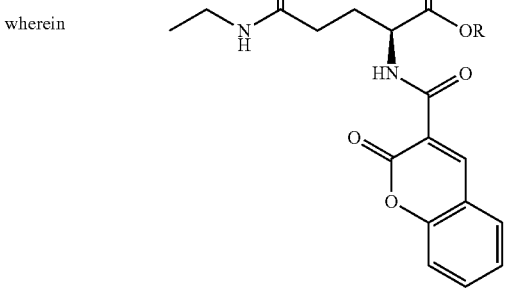

wherein
according to the formula and procedures above.

3. A method for preparing a compound as represented by formula (I):

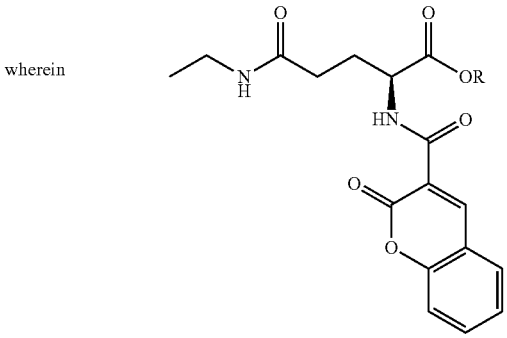

Formula (I)

wherein Formula (I) has variables and bonds selected from (Ie) to (Ih), wherein;
R=CH$_2$CH$_3$, and (Ic) R$_1$=Cl, R$_2$=H and ⁓⁓⁓ = ◄━━ ;
(Id) R$_1$=Br, R$_2$=H and ⁓⁓⁓ = ◄━━ ;
(Ie) R$_1$=F, R$_2$=H and ⁓⁓⁓ = ·····⫿⫿⫿⫿ ;
(If) R$_1$=NO$_2$, R$_2$=H and ⁓⁓⁓ = ·····⫿⫿⫿⫿ ;
(Ig) R$_1$=Cl, R$_2$=Cl and ⁓⁓⁓ = ◄━━ ;
(Ih) R$_1$=Br, R$_2$=Br and ⁓⁓⁓ = ◄━━ ;

comprising:
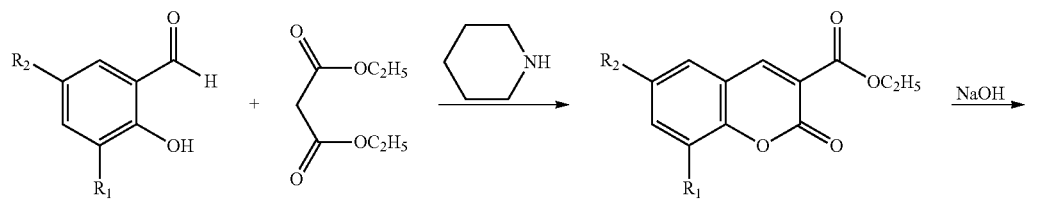
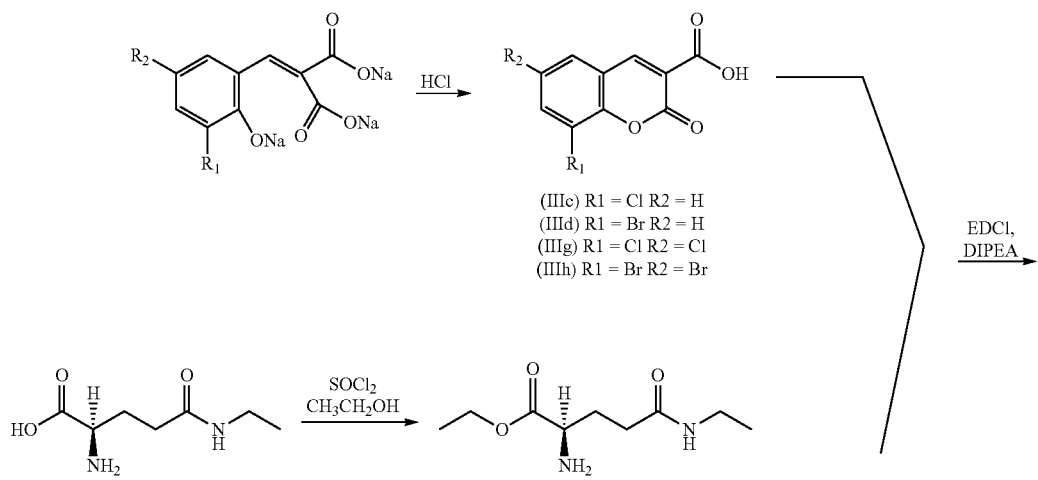
(IIIc) R1 = Cl R2 = H
(IIId) R1 = Br R2 = H
(IIIg) R1 = Cl R2 = Cl
(IIIh) R1 = Br R2 = Br
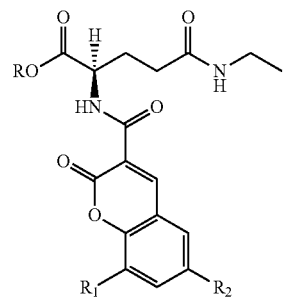
(Ic) R = CH2CH3 R1 = Cl R2 = H
(Id) R = CH2CH3 R1 = Br R2 = H
(Ig) R = CH2CH3 R1 = Cl R2 = Cl
(Ih) R = CH2CH3 R1 = Br R2 = Br
or alternatively comprising:
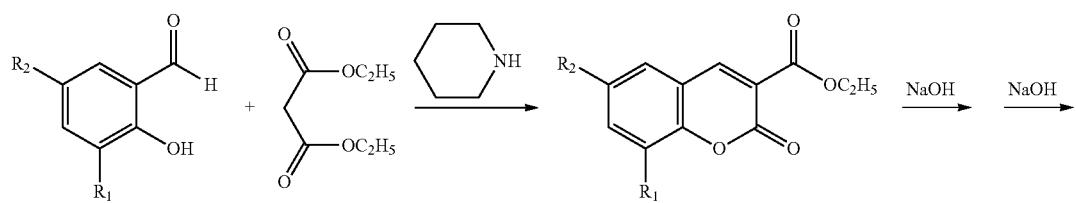

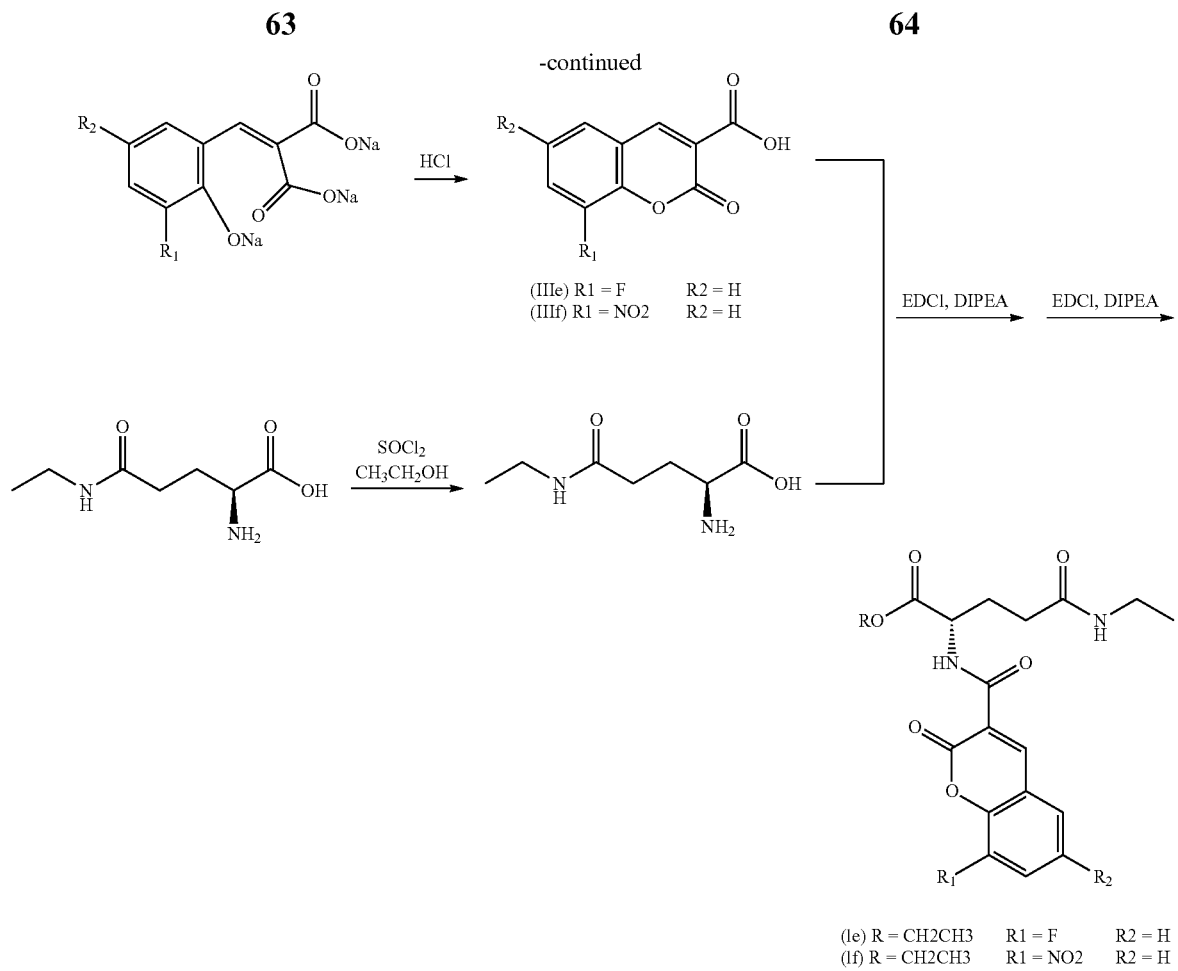

according to the formula and procedures above.

4. A pharmaceutical composition, comprising a compound according to claim 1 and optionally, a pharmaceutically acceptable excipient.

5. A pharmaceutical composition comprising a compound as represented by formula (I):

Formula (I)

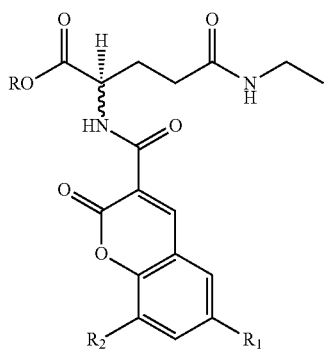

wherein Formula (I) has variables and bonds selected from (Ib) to (Ii), wherein
R=CH$_2$CH$_3$, and
(Ib) R$_1$=H, R$_2$=H and ⌇⌇ = ⋯⋯‖‖‖ ;
(Ic) R$_1$=Cl, R$_2$=H and ⌇⌇ = ◣ ;
(Id) R$_1$=Br, R$_2$=H and ⌇⌇ = ◣ ;
(Ie) R$_1$=F, R$_2$=H and ⌇⌇ = ⋯⋯‖‖‖ ;
(If) R$_1$=NO$_2$, R$_2$=H and ⌇⌇ = ⋯⋯‖‖‖ ;
(Ig) R$_1$=Cl, R$_2$=Cl and ⌇⌇ = ◣ ;
(Ih) R$_1$=Br, R$_2$=Br and ⌇⌇ = ◣ ; or
(Ii) R$_1$=NH$_2$, R$_2$=H ⌇⌇ and ⋯⋯‖‖‖ ,
and a pharmaceutically acceptable excipient wherein the pharmaceutical composition is in the forms of deglutible tablets, buccal tablets, troches, capsules, elixirs, suspensions, syrups, wafers, injection, spreadable pastes, gels, ointments or soaps, emulsive liposomes, microspheres and nanospheres.

6. A method for treating a patient with human cancer, comprising administering to the patient to be treated a therapeutically effective amount of the compound according to claim 1, or the pharmaceutical composition of claim 5.

7. A method for inhibiting histone methyltransferase EZH2, in a patient suffering from cancer comprising administering the compound according to claim 1, or the pharmaceutical composition of claim 5.

8. The method according to claim 6, wherein the human cancer is in the form of tumors.

9. A method for treatment of tumors in synergy with radiotherapy, or in cooperation with radiotherapy, chemotherapy, surgical treatment, thermal therapy, and multimodality therapy, comprising administering to the subject in need a therapeutically effective amount of the compound according to claim 1 or the pharmaceutical composition of claim 5.

* * * * *